(12) United States Patent
Swartz et al.

(10) Patent No.: US 8,481,045 B2
(45) Date of Patent: Jul. 9, 2013

(54) IMMUNOGENIC PROTEIN CONSTRUCTS

(75) Inventors: James Robert Swartz, Menlo Park, CA (US); Junhao Yang, Palo Alto, CA (US); Alexei M. Voloshin, Newark, CA (US); Ronald Levy, Stanford, CA (US); Gregg Kanter, Boston, MA (US); Shoshana Levy, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/687,653

(22) Filed: Jan. 14, 2010

(65) Prior Publication Data

US 2010/0183655 A1 Jul. 22, 2010

Related U.S. Application Data

(63) Continuation of application No. 12/305,619, filed as application No. PCT/US2007/015220 on Jun. 28, 2007, now abandoned.

(60) Provisional application No. 60/817,442, filed on Jun. 28, 2006, provisional application No. 60/817,522, filed on Jun. 28, 2006.

(51) Int. Cl.
*A61K 39/145* (2006.01)
*C07K 14/005* (2006.01)

(52) U.S. Cl.
USPC ............... 424/190.1; 424/209.1; 424/184.1; 530/350

(58) Field of Classification Search
None
See application file for complete search history.

(56) References Cited

U.S. PATENT DOCUMENTS

| 5,747,309 | A | * | 5/1998 | Allan et al. ............. 424/93.4 |
| 6,337,191 | B1 | | 1/2002 | Swartz et al. |
| 6,740,325 | B1 | * | 5/2004 | Arnon et al. ............. 424/206.1 |
| 2004/0209321 | A1 | | 10/2004 | Swartz et al. |
| 2005/0054032 | A1 | | 3/2005 | Voloshin et al. |
| 2005/0054044 | A1 | | 3/2005 | Swartz et al. |
| 2009/0233343 | A1 | * | 9/2009 | Kleanthous et al. ......... 435/174 |

FOREIGN PATENT DOCUMENTS

| WO | 01/32871 | 5/2001 |
| WO | 2004/016778 | 2/2004 |
| WO | 2005/052117 | 6/2005 |
| WO | WO 2006/097708 A2 * | 9/2006 |

OTHER PUBLICATIONS

Farkas-Himsley et al. (PNAS 1995, vol. 92, p. 6996-7000).*
Ferguson et al. JMB, 2001, vol. 207, p. 393-405).*
Osborne et al., (Biochemistry 1996, vol. 35, p. 9505-9512).*
Calhoun; et al., "Energizing Cell-Free Protein Synthesis with Glucose Metabolism", Biotechnology and Bioengineering (2005), 90(5):606-613.
Ferguson; et al., "Rapid Folding with and without Populated Intermediates in the Homologous Four-helix Proteins Im7 and Im9", JMB (1999), 286:1597-1608.
Jewett; et al., "Mimicking the *Escherichia coli* Cytoplasmic Environment Activates Long-Lived and Efficient Cell-Free Protein Synthesis", Biotechnology and Bioengineering (2004), 86(1):19-25.
Jewett; et al., "Prokaryotic Systems for In Vitro Expression", Gene Cloning and Expression Technologies (2002), p. 391-411.
Lin; et al., "Genetic Reconstruction of the Aerobic Central Metabolism in *Escherichia coli* for the Absolute Aerobic Production of Succinate", Biotechnology and Bioengineering (2004), 89(2):148-56.
Liu; et al., "Streamlining *Escherichia coli* S30 Extract Preparation for Economical Cell-Free Protein Synthesis", Biotechnol. Prog. (2005), 21:460-465.
Rohm; et al., "Characterization of a Novel Influenza Hemagglutinin, H15: Criteria for Determination of Influenza A Subtypes", Virology (1996), 217:508-516.
Zawada; et al., "Effects of Growth Rate on Cell Extract Performance in Cell-Free Protein Synthesis", Biotechnology and Bioengineering (2006), 94(4):618-24.

* cited by examiner

*Primary Examiner* — Agnieszka Boesen
(74) *Attorney, Agent, or Firm* — Bozicevic, Field & Francis LLP; Pamela J. Sherwood

(57) ABSTRACT

Bacterial immunity proteins are utilized to increase immune response to an antigen of interest.

8 Claims, 8 Drawing Sheets

US 8,481,045 B2

IMMUNOGENIC PROTEIN CONSTRUCTS

FEDERALLY SPONSORED RESEARCH AND DEVELOPMENT

Figure 1:
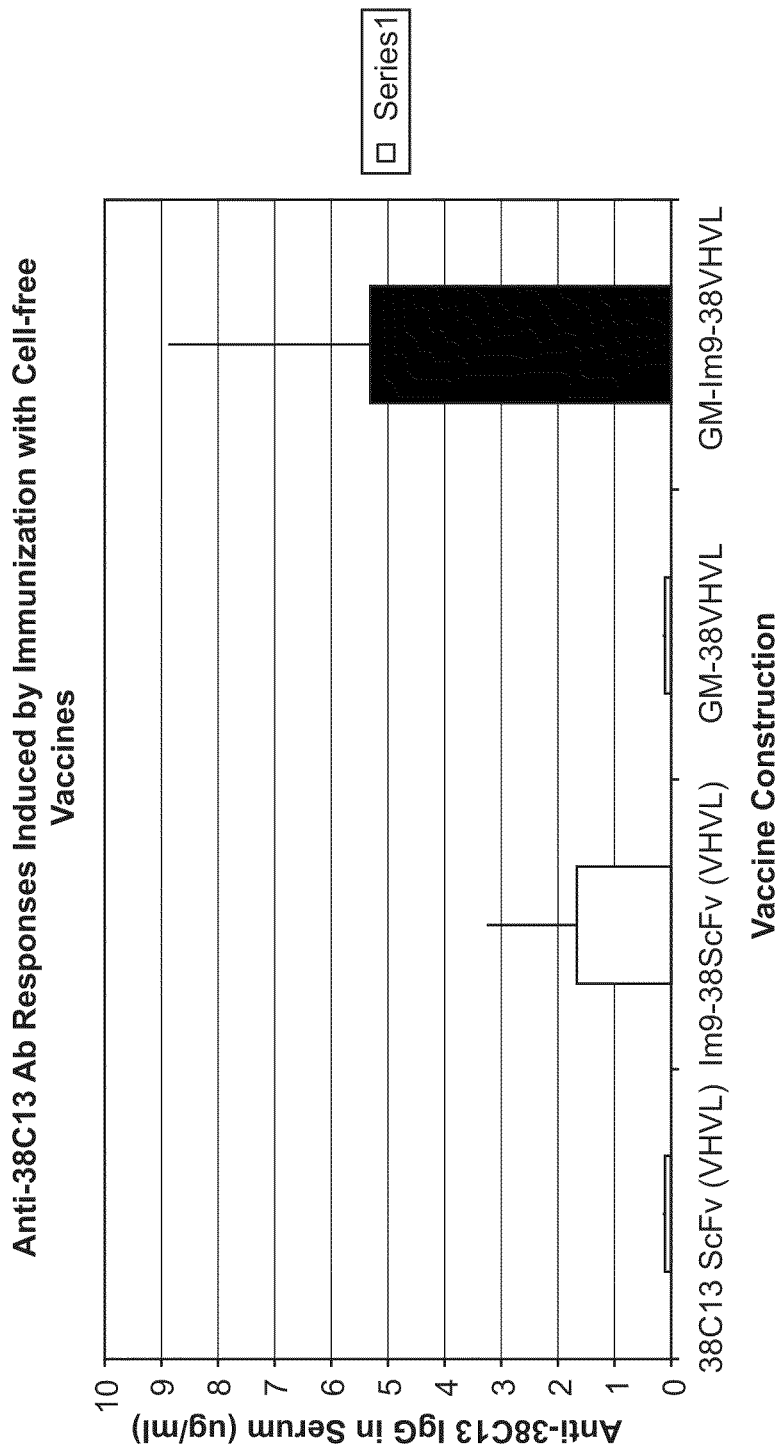
Figure 2:
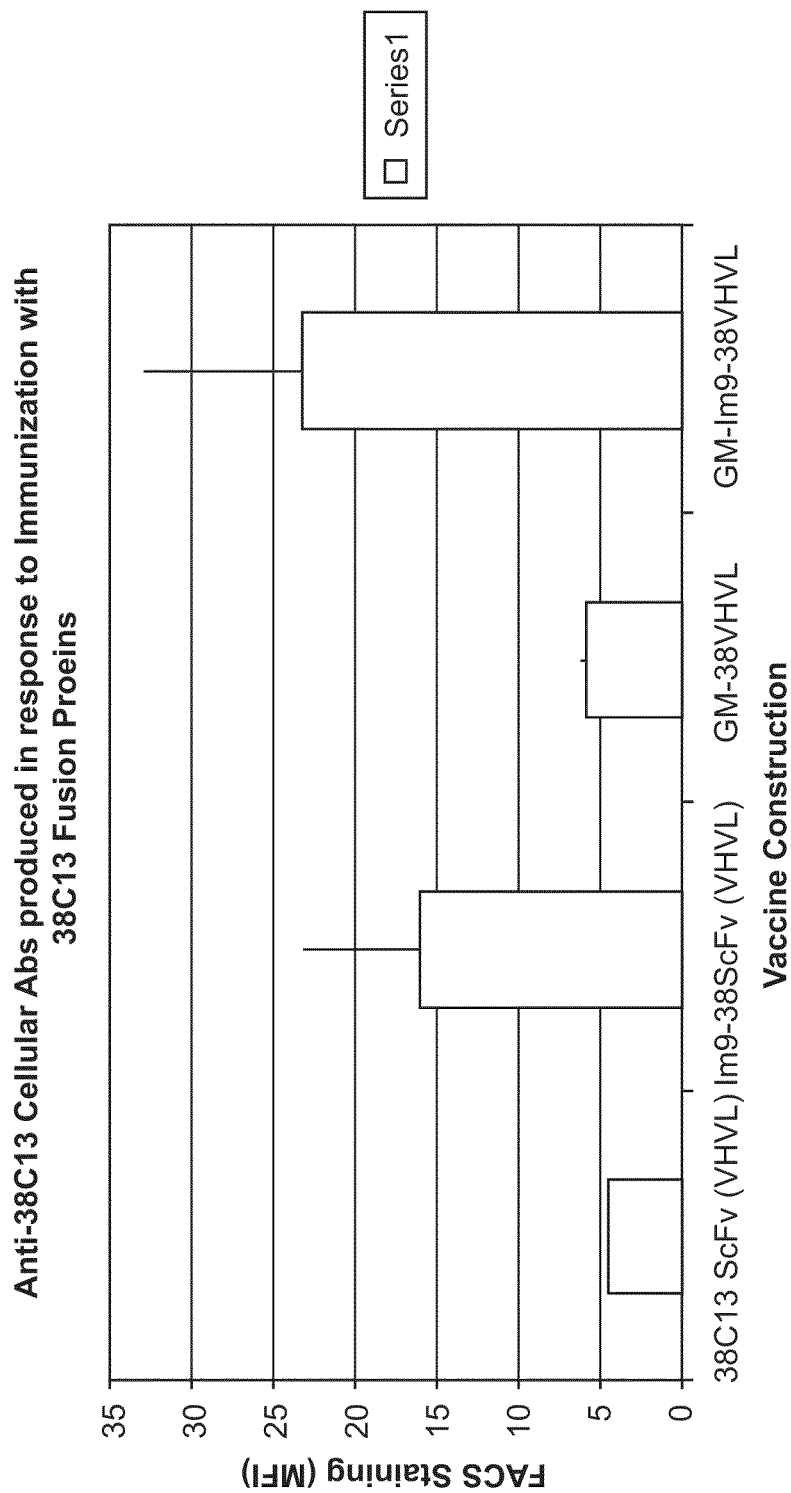
Figure 3:
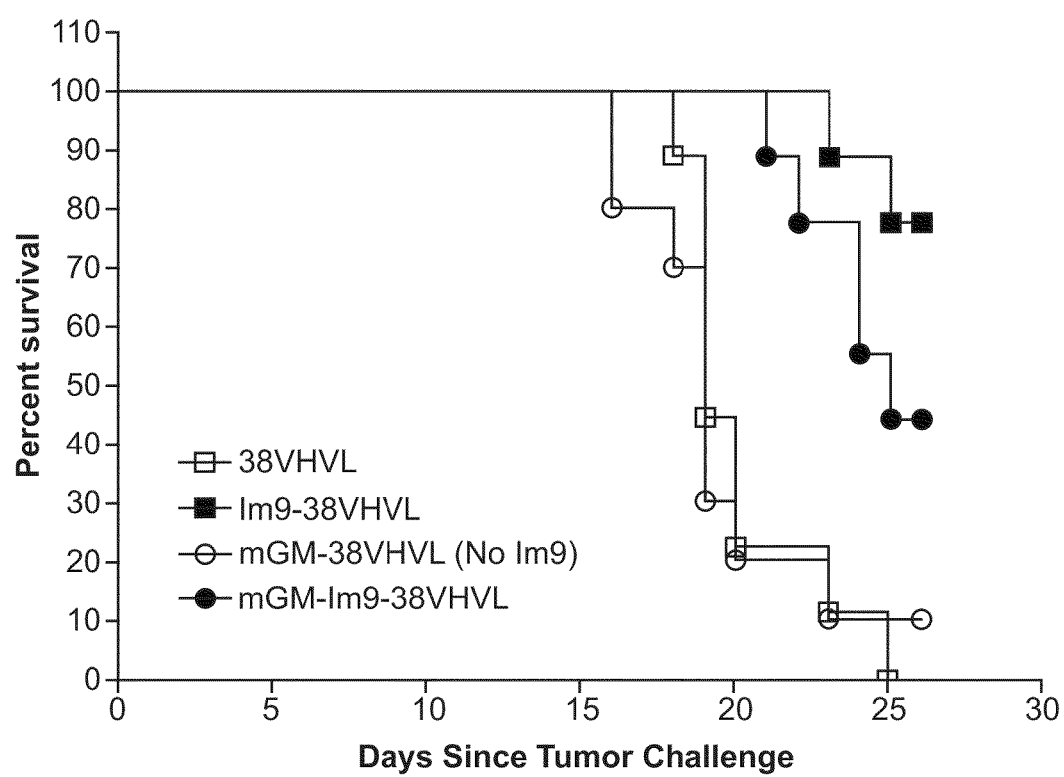

This invention was made with Government support under contract CA034233 awarded by the National Institutes of Health. The Government has certain rights in this invention.

BACKGROUND OF THE INVENTION

Many cellular processes involve proteins with multiple domains. This modular nature of proteins provides many advantages, providing increased stability and new cooperative functions. In addition, chimeric proteins that provide for new functional combinations can be designed from domain modules of different proteins.

The amino acid linkers that join domains can play an important role in the structure and function of multi-domain proteins. There are numerous examples of proteins whose catalytic activity requires proper linker composition. In general, altering the length of linkers connecting domains has been shown to affect protein stability, folding rates and domain-domain orientation (see George and Hering a (2003) Prot. Eng. 15:871-879). The use of linkers in the rational design of functional proteins is of interest for many purposes.

Immune responses to resolve different pathologies, such as those seen in viral infections, bacterial infections, cancer, and allergic reactions are important to the overall health of the host. Successful resolution of infections, cancer, or allergic reactions may depend on the type and magnitude of the immune response. Immunizations, whereby antigen is used to elicit further immune responses, may be helpful in successfully resolving the infections, cancers, and/or allergic reactions. It would be desirable to have a method of immunization that would enable the immune system to address all the aforementioned infections and diseases.

While vaccination protocols have been some of the great medical achievements in the last century, there are still conditions where an effective immune response has been difficult to generate. For example, human tumor immunotherapy has met with only limited success. Among the reasons for this has been the limited availability of tumor-associated antigens, and an inability to deliver such antigens in a manner that renders them immunogenic. In other instances, the need for a fast immune response is not met by current vaccine technology.

In the continual pursuit for safer and more effective vaccines, new technologies, including recombinant, purification and synthetic methods, have been used to improve the quality and specificity of antigens used. Purified, sub-unit and synthesized antigens demonstrate increased safety but diminished immunogenicity, which has been one driver for identification of effective adjuvants. Adjuvants are generally compounds, that when administered with an antigen (either in conjunction with, or given prior to the administration of the antigen) enhances and/or modifies the immune response to that particular antigen.

The present invention provides novel immunogenic compositions that exhibit improved immunogenicity; and methods of use of such compositions.

Relevant Literature

U.S. Pat. No. 6,337,191 B1; Swartz et al. U.S. Patent Published Application 20040209321; Swartz et al. International Published Application WO 2004/016778; Swartz et al. U.S. Patent Published Application 2005-0054032-A1; Swartz et al. U.S. Patent Published Application 2005-0054044-A1; Swartz et al. International Published Application WO 2005/052117. Calhoun and Swartz (2005) Biotechnol Bioeng 90(5):606-13; Jewett and Swartz (2004) Biotechnol Bioeng 86(1):19-26; Jewett et al. (2002) Prokaryotic Systems for In Vitro Expression. In: Weiner M, Lu Q, editors. Gene cloning and expression technologies. Westborough, Mass.: Eaton Publishing. p 391-411; Lin et al. (2005) Biotechnol Bioeng 89(2):148-56; Liu et al., 2005 Biotechnol Prog 21:460-465; Jewett M C and Swartz J R, 2004 Biotechnol Prog 20:102-109; Zawada and Swartz Biotechnol Bioeng, 2006. 94(4): p. 618-24.

The Im9 protein sequence is deposited at Genbank, accession number CAA33863. The structure of the protein is disclosed by Ferguson et al. (1999) J. Mol. Biol. 286:1597-1608.

Rohm et al. (1996) Virology, 217, 508-516 discusses characterization of an influenza hemaglutinin.

SUMMARY OF THE INVENTION

Polypeptide compositions that increase immunogenicity, and methods of use thereof are provided, where the immune response of a mammalian host to an antigen of interest is increased by co-formulation of the antigen with a bacterial immunity protein.

In one embodiment of the invention, a bacterial immunity protein is administered in a formulation with an antigenic compound, where the antigenic compound and the immunity protein are present as separate molecules. The immunity protein acts as an adjuvant to increase immune response to the antigenic compound.

In another embodiment, an antigenic formulation, e.g. a vaccine, comprises a bacterial immunity protein present in a fusion protein with an antigenic polypeptide. The immunity protein may be used as a linker to join two domains of the fusion protein, or may be provided at the amino or carboxy terminus of the fusion protein.

In some embodiments of the invention, an influenza virus hemagglutinin (HA) is fused to one or more immunostimulatory proteins, e.g. IL-1β, GM-CSF, etc. through a bacterial immunity protein. In some embodiments, the influenza virus is an influenza A virus. The fusion proteins can be made by transforming host cells with nucleic acid encoding the fusion, culturing the host cell and recovering the fusion from the culture, or alternatively by generating a nucleic acid construct encoding the fusion and producing the polypeptide by cell free synthesis, which synthesis may include coupled transcription and translation reactions. Also provided are vectors and polynucleotides encoding the fusion protein.

BRIEF DESCRIPTION OF THE DRAWINGS

FIG. 1. Ab Responses to Vaccines Following 3 Vaccinations with Cell Free Proteins, as measured by ELISA.

FIG. 2. Ab Responses to Vaccines Following 3 Vaccinations with Cell Free Proteins, as measured by Flow Cytometry.

FIG. 3. Mouse Survival in Response to Challenge with 1200 38C13 Tumor Cells after 3 Vaccinations With Cell-Free Proteins.

FIG. 4. Constructs of HA fusion proteins

FIG. 5. Expression data for HA Hong Kong related constructs

FIG. 6. Expression data at 30 C for HA Viet Nam related constructs

FIG. 7. Coomassie blue stained PAGE gels showing fractions from a His Trap column purification of the H4 fusion protein product

Figure 8:
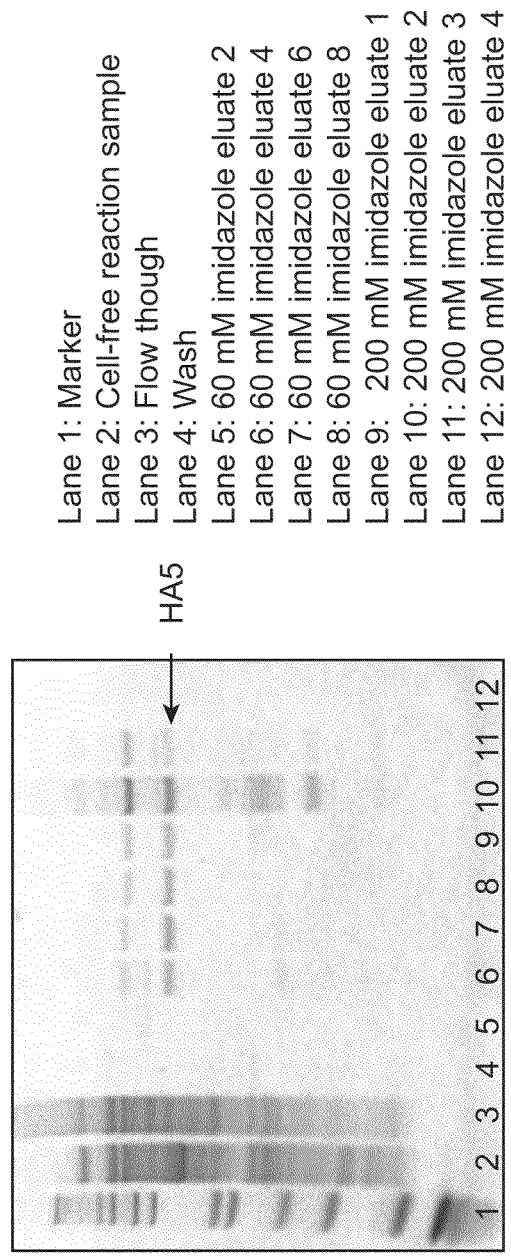

FIG. 8. Coomassie blue stained PAGE gels showing fractions from a HisTrap column purification of the H5 fusion protein product

DETAILED DESCRIPTION OF THE EMBODIMENTS

The present invention is directed to immunogenic compositions and methods useful for the induction and/or enhancement of an immune response, which may be humoral and/or cell-mediated, in a human, a non-human animal, or cell culture, usually in a mammalian host. Immunogenic compositions of the invention comprise a bacterial immunity protein as described herein; and an antigenic compound, which may be a polypeptide antigen. The bacterial immunity protein is optionally covalently bound to the polypeptide antigen. The presence of the bacterial immunity protein enhances the immune response to the antigen. The bacterial immunity protein may enhance an immune response by affecting, for example, the type and quantity of cellular responses, and/or of immunoglobulins, chemokines, and/or cytokines produced. The innate immunity, humoral and/or cell-mediated immune responses are more effective with the presence of the linker.

In some embodiments, the specific titer of antibodies raised in a mammalian host to an immunogen is increased at least about 20% when the immunogen is delivered with a bacterial immunity protein, as compared to the immunogen when delivered by the same route, in the absence of the bacterial immunity protein. In other embodiments, the specific titer is increased as least about 30%, at least about 40%, at least about 50%, at least about 75%, at least about 100%, or more. The immunostimulatory activity of bacterial immune proteins is surprising. Bacterial immunity proteins protect bacteriocin-producing organisms against the antimicrobial activity of their own bacteriocin, typically by binding to the toxin and neutralizing it, and are functionally unrelated to mammalian immunoregulatory proteins.

An antigenic composition of the invention comprises a bacterial immunity protein, as set forth herein. The bacterial immunity protein may be present in a multi-domain fusion protein, where the immunity protein bridges two domains of the fusion protein. The immunity protein linker may be used alone or in combination with an additional flexible linker sequence, and may also comprise a tag for purification. Alternatively, the bacterial immunity protein may be provided in a composition with an antigenic compound, where the two are not covalently joined. In another embodiment, the bacterial immunity protein is covalently joined to an immunogenic polypeptide at the terminus of the polypeptide.

The fusion proteins of this invention can be made by transforming host cells with nucleic acid encoding the fusion, culturing the host cell and recovering the fusion from the culture, or alternatively by generating a nucleic acid construct encoding the fusion and producing the polypeptide by cell free synthesis, which synthesis may include coupled transcription and translation reactions.

Proteins for use in the invention may be purified and formulated in pharmacologically acceptable vehicles for administration to a patient. In one embodiment of the invention the fusion protein comprises at least one domain of an immunoglobulin, e.g. a variable region domain; a constant region domain; a single chain Fv fragment; etc. Such fusion proteins find use, for example, as vaccines for the treatment of B cell lymphomas.

Examples of an immune response that can be enhanced by the method of the invention include, but are not limited to, activation of innate immunity (e.g., macrophages, natural killer (NK) cells), a Th1 response, a cytotoxic T lymphocyte (CTL) response, and production of an antibody, including increased production of antibodies of the IgG classes, e.g. IgG1, IgG2A, IgG2B, IgG3 and IgG4. The method can be used for immunizing a subject against an antigen and provides more effective immunization than if the antigen were similarly administered in the absence of the linker. The method can be used prophylactically or therapeutically.

Definitions

As used herein, the term "antigenic compound" refers to any substance that can be recognized by the immune system (e.g., bound by an antibody or processed so as to elicit a cellular immune response) under appropriate conditions.

An "antigen" as used herein includes but is not limited to cells; cell extracts; proteins; lipoproteins; glycoproteins; nucleoproteins; polypeptides; peptides; polysaccharides; polysaccharide conjugates; peptide mimics of polysaccharides; lipids; glycolipids; carbohydrates; viruses; viral extracts; bacteria; bacterial extracts; fungi; fungal extracts; multicellular organisms such as parasites; and allergens. In some embodiments of the invention the antigen is a polypeptide, e.g. a native polypeptide; a polypeptide produced by recombinant methods, including in vitro cell free synthesis, bacterial and prokaryotic expression systems; and the like. Such antigens include, without limitation, viral antigens derived from HIV; influenza, smallpox (vaccinia), measles, mumps, rubella, poliovirus, rotavirus, varicella (chickenpox), hepatitis A, B, C, D virus, bacterial antigens, tumor antigens, and the like. Bacterial antigens of interest include, without limitation, antigens derived from *Bacillus anthracis; Bordetella pertussis, Clostridium tetani, Haemophilus Influenzae, Corynebacterium diphtheriae, Meningococcus* sp., *Streptococcus pneumoniae, Salmonella typhi, Mycobacterium tuberculosis*, etc.

Antigens may be exogenous (e.g., from a source other than the individual to whom the antigen is administered, e.g., from a different species) or endogenous (e.g., originating from within the host, e.g., a diseased element of body, a cancer antigen, a virus infected cell producing antigen, and the like). Antigens may be native (e.g., naturally-occurring); synthetic; or recombinant. Antigens include crude extracts; whole cells; and purified antigens, where "purified" indicates that the antigen is in a form that is enriched relative to the environment in which the antigen normally occurs and/or relative to the crude extract, for example, a cultured form of the antigen.

Influenza HA protein. The genome of the influenza A virus (family Orthomyxoviridae) consists of eight single-stranded negative sense RNA molecules spanning approximately 13.5 kilobases (kb). The segments range in length from 890 to 2,341 nucleotides and encode a total of 11 proteins. The hemagglutinin (HA) and neuraminidase (NA) segments of the genome encode the two main surface proteins, and are the source of most of the antigenic variation in the virus.

The influenza virus population may contain multiple lineages at any given time. The sequences of HA proteins are known in the art, and extensive sequence variation is publicly available. For example, more than 200 influenza genomes were published by Ghedin et al. (2005) Nature 437(7062): 1162-6, "Large-scale sequencing of human influenza reveals the dynamic nature of viral genome evolution"; and Holmes et al. (2005) PLoS Biol. 3(9):e300 "Whole-genome analysis of human influenza A virus reveals multiple persistent lineages and reassortment among recent $H_3N_2$ viruses", each of which is herein specifically incorporated by reference for the teachings of sequences encoding HA proteins. The term influenza HA protein additionally refers to truncated fragments of the HA protein which may comprise the sialic binding domain or the entire extracellular domain, for example.

In some embodiments of the invention, a cytokine is included in a fusion protein with an immunogen and bacterial immunity protein. The term "cytokine" is a generic term for proteins released by one cell population which act on another cell as intercellular mediators. Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen, OB protein; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha. and TGF-.beta.; insulin-like growth factor-I and -II; erythropoietin (EPO); osteoinductive factors; interferons such as interferon-.alpha., -$\beta$ and -$\gamma$; colony stimulatingfactors (CSFs) such as macrophage-CSF(M-CS F); granulocyte-macrophage-CSF(GM-CSF); and granulocyte-CSF (G-CSF); interleukins (ILs) such as IL-1, IL-1$\alpha$, IL-2, IL-3, IL-4, IL-5, IL-6, IL-7, IL-8, IL-9, IL-11, IL-12; and other polypeptide factors including leukemia inhibitory factor (LIF) and kit ligand (KL). As used herein, the term cytokine includes proteins from natural sources or from recombinant cell culture and biologically active equivalents of the native sequence cytokines.

Immunomodulatory proteins of interest include colony stimulating factors (CSFs), which are proteins necessary for the survival, proliferation, and differentiation of hematopoietic progenitor cells. They are named by the cells they stimulate. Macrophage CSF is known as CSF1. Granulocyte-macrophage CSF (CSF2, also symbolized GMCSF) stimulates both cell types. Multi-CSF is known as interleukin-3 (IL3; 147740). GM-CSF is a glycoprotein of MW 45,000 and is a homodimer. Wong et al. (1985) isolated cDNA clones for human GMCSF. A sequence of human GM-CSF may be found in Wong et al. (1985) Science 228: 810-815, herein incorporated by reference.

IL-1$\beta$. Interleukin-1, produced mainly by blood monocytes, mediates the panoply of host reactions collectively known as acute phase response. It is identical to endogenous pyrogen. The multiple biologic activities that define IL1 are properties of a 15- to 18-kD protein that is derived from a 30- to 35-kD precursor. IL-1 sequences are available at. for example, Auron et al. (1984) Proc. Nat. Acad. Sci. 81: 7907-7911; Cameron et al. (1985) J. Exp. Med. 162: 790-801; and March et al. (1985) Nature 315: 641-647, each herein incorporated by reference.

An "immunogenic composition" as used here in refers to a combination of two or more substances (e.g., an antigen and an immune enhancing linker) that together elicit an immune response when administered to a host.

The term "polypeptide," "peptide," "oligopeptide," and "protein," are used interchangeably herein, and refer to a polymeric form of amino acids of any length, which can include coded and non-coded amino acids, chemically, or biochemically modified or derivatized amino acids, and polypeptides having modified peptide backbones.

An "effective amount of an antigenic compound" refers to an amount of antigenic compound which, in optional combination with an adjuvant, will cause the subject to produce a specific immunological response to the antigenic compound.

The term "immune response" refers to any response to an antigenic or immunogenic compound by the immune system of a vertebrate subject. Exemplary immune responses include, but are not limited to local and systemic cellular as well as humoral immunity, such as cytotoxic T lymphocytes (CTL) responses, including antigen-specific induction of CD8$^+$ CTLs, helper T-cell responses including T-cell proliferative responses and cytokine release, and B-cell responses including antibody response.

The term "eliciting an immune response" is used herein generally to encompass induction and/or potentiation of an immune response.

The term "inducing an immune response" refers to an immune response that is stimulated, initiated, or induced.

The term "potentiating an immune response" refers to a pre-existing immune response that is improved, furthered, supplemented, amplified, enhanced, increased or prolonged.

The expression "enhanced immune response" or similar means that the immune response is elevated, improved or enhanced to the benefit of the host relative to the prior immune response status, for example, before the administration of an immunogenic composition of the invention.

The terms "humoral immunity" and "humoral immune response" refer to the form of immunity in which antibody molecules are produced in response to antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response normally includes lymphocyte proliferation. When "lymphocyte proliferation" is measured, the ability of lymphocytes to proliferate in response to a specific antigen is measured. Lymphocyte proliferation is meant to refer to B cell, T-helper cell or cytotoxic T-lymphocyte (CTL) cell proliferation.

The term "immunogenic amount" refers to an amount of antigenic compound sufficient to stimulate an immune response, when administered with a subject immunogenic composition, as compared with the immune response elicited by the antigen in the absence of the polynucleotide adjuvant.

The term "immunopotentiating amount" refers to the amount of the adjuvant needed to effect an increase in antibody titer and/or cell-mediated immunity when administered with an antigenic compound in a composition of the invention, as compared with the increase in antibody and/or cell mediated immunity level observed in the absence of the polynucleotide adjuvant.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, particularly a mammalian subject, more particularly a human, and includes: (a) preventing the disease or symptom from occurring in a subject which may be predisposed to the disease or symptom but has not yet been diagnosed as having it; (b) inhibiting the disease symptom, e.g., arresting its development; or relieving the disease symptom, i.e., causing regression of the disease or symptom (c) reduction of a level of a product produced by the infectious agent of a disease (e.g., a toxin, an antigen, and the like); and (d) reducing an undesired physiological response to the infectious agent of a disease (e.g., fever, tissue edema, and the like).

Bacterial Immunity Proteins

Exemplary bacterial immunity proteins include colicin binding proteins, which can be obtained from various species of Enterobacteriaceae, including *E. coli, Pseudomonas* sp., *Salmonella*, sp., *Yersinia*, sp., *Klebsiella* sp., etc. Many of these proteins are plasmid encoded. The polypeptide sequences have some sequence identity to each other, e.g. an immunity protein of interest may have at least about 40%, at least about 50%, at least about 60%, at least about 70%, at least about 80%, at least about 90%, at least about 95% or more sequence identity at the amino acid level to *E. coli* Im9. Preferred proteins are at least about 45 amino acids in length, more usually at least about 55 amino acids in length and not more than about 100 amino acids in length, not more than about 95 amino acids in length, or not more than about 90 amino acids in length.

Immunity proteins can also be characterized by their structure. The proteins adopt a distorted, anti-parallel four-helical structure with an all α-helical topology (see Ferguson et al. (1999) JMB 286:1597-1608, herein specifically incorporated by reference), and lack disulphide bonds and prosthetic groups in the native state.

Immunity proteins are typically able to fold into a thermodynamically stable structure with reaction durations typically shorter than about 10 seconds as determined by optimized in vitro refolding reactions; and are generally comprised of multiple alpha helices, having at least about two, at least about three, usually at least about 4 alpha helices. Methods for prediction of folding rates may be found, inter alia, in Debe and Goddard (1999) J Mol Biol. 294(3):619-25, herein specifically incorporated by reference.

The presence of alpha helices in a sequence can be empirically determined, e.g. by CD spectra, where a polypeptide retains CD spectra characteristic of an alpha helix, and where the characteristic spectra persists in the presence of up to 2 M urea. Methods relating to spectral analysis of tertiary structures in polypeptides may be found, inter alia, in Turner et al. J Phys Chem B. 2007 Feb. 22; 111(7):1834; Shepherd et al. J Am Chem. Soc. 2005 Mar. 9; 127(9):2974-83; Thulstrup et al. Biopolymers. 2005 May; 78(1):46-52; Jeong et al. Mol Cells. 2004 Feb. 29; 17(1):62-6; Maiti et al. J Am Chem Soc. 2004 Mar. 3; 126(8):2399-408; Maeda et al. J Pept Sci. 2003 February; 9(2):106-13; Verzola et al. Electrophoresis. 2003 March; 24(5):794-800; Wallimann et al. J Am Chem Soc. 2003 125(5):1203-20; Lawrence et al. Biophys Chem. 2002 Dec. 10; 101-102:375-85, herein specifically incorporated by reference.

The presence of alpha helical structure can also be predicted based on the amino acid sequence, e.g. as described by Phoenix et al. Curr Protein Pept Sci. 2002 April; 3(2):201-21; Muñoz et al. Curr Opin Biotechnol. 1995 August; 6(4):382-6; Godzik et al. J Comput Aided Mol. Des. 1993 August; 7(4): 397-438; Viswanadhan et al. Biochemistry. 1991 Nov. 19; 30(46):11164-72; Garnier et al. Biochem Soc Symp. 1990; 57:11-24, herein specifically incorporated by reference.

Bacterial immunity proteins include colicin binding proteins, which can be obtained from various species of Enterobacteriaceae, including *E. coli, Pseudomonas* sp., *Salmonella*, sp., *Yersinia*, sp., *Klebsiella* sp., etc. Many of these proteins are plasmid encoded. The polypeptide sequences have a sequence identity to each other, e.g. an immunity protein of interest may have at least about 40%, at least about 50%, at least about 60%, at least about 70%, at least about 80%, at least about 90%, at least about 95% sequence identity to a polypeptide or more sequence identity at the amino acid level to a polypeptide sequence set forth in SEQ ID NO:1-15.

Immunity proteins can also be characterized by their structure. The proteins adopt a distorted, antiparallel four-helical structure with an all α-helical topology (see Ferguson et al. (1999) JMB 286:1597-1608, herein specifically incorporated by reference); lack disulphide bonds and prosthetic groups and may lack cis-Xaa prolyl peptide bonds in the native state.

In certain embodiments, an immunity protein is a polypeptide of from about 55 to about 90 amino acids in length, which will fold into a thermodynamically stable structure from a linear form in less than about 10 seconds as determined by optimized in vitro refolding reactions.

In certain embodiments, the linker of the present invention is a polypeptide of from about 55 to about 90 amino acids in length, having 4 α helices in a distorted, antiparallel four-helical structure, and lacking disulphide bonds.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

Immunity Proteins

| Sequence identifier | Organism | Gene | Genbank | SEQUENCE |
|---|---|---|---|---|
| SEQ ID NO: 1 | E. coli | Im9 | CAA33863 | ELKHSISDYTEAEFLQLVTTICNADTSSEEELVKLVTHFEEMTE HPSGSDLIYYPKEGDDDSPSGIVNTVKQWRAANGKSGFKQG |
| SEQ ID NO: 2 | E. coli | Im6 | X15856 | GLKLHINWFDKRTEEFKGGEYSKDFGDDGSVIERLGMPFKDNIN NGWFDVIAEWVPLLQPYFNHQIDISDNEYFVSFDYRDGDW |
| SEQ ID NO: 3 | E. coli | Im5 | X15857 | KLSPKAAIEVCNEAAKKGLWILGIDGGHWLNPGFRIDSSASWTY DMPEEYKSKIPENNRLAIENIKDDIENGYTAFIITLKM |
| SEQ ID NO: 4 | E. coli | immHu194 | | ELKHSISDYTEAEFLEFVKKICRAEGATEEDDNKLVREFERLTE HPDGSDLIYYPRDDREDSPEGIVKEIKEWRAANGKPGFKQG |
| SEQ ID NO: 5 | E. coli | Im7 | 1AYI | ELKNSISDYTEAEFVQLLKEIEKENVAATDDVLDVLLEHFVKIT EHPDGTDLIYYPSDNRDDSPEGIVKEIKEWRAANGKPGFKQG |
| SEQ ID NO: 6 | Y. pestis | | | KFIQDVEENKMELKEKYEDYTEHEFLEFIRNICEVNTDSQSLHS SWVRHFTKITEHPSGSDLIYYPEDGADDSPEGILELVKKWRAEN GKPGFKK |
| SEQ ID NO: 7 | E. coli | immE8 | AAA23074 | ELKNSISDYTETEFKKIIEDIINCEGDEKKQDDNLEHFISVTEH PSGSDLIYYPEGNNDGSPEAVIKEIKEWRAANGKSGFKQG |
| SEQ ID NO: 8 | Photorhabdus luminescens | | CAE14186 | KLNKKLEDYTEAEFLEFARKVCNADYATEDEANVAVQDFIRLSE HPDGTDLFYPSSGQDDSPEGIVKQIKEWRAKSGKPGFKK |
| SEQ ID NO: 9 | Klebsleiia pneumoniae | kbi | NP_068717 | ANKTLADYTEQEFIEFIEKIKKADFATESEHDEAIYEFSQLTEH PDGWDLIYHPQAGADNSPAGVVKTVKEWRAANGKPGFKKS |
| SEQ ID NO: 10 | Yersinia pseudotuberculosis | pyocin S2 immunity protein | CAH19391 | EDKSICDYTESEFLELVKELFNVEKTTEEEDINNLIEFKRLCEH PAGSDLIFYPDNNREDSPEGVVKEVKKWRAENGKPGFKK |
| SEQ ID NO: 11 | Pseudomonas aeruginosa | pyocin S1 immunity protein | BAA02202 | KSKISEYTEKEFLEFVEDIYTNNKKKFPTEESHIQAVLEFKKLT EHPSGSDLLYYPNENREDSPAGVVKEVKEWRASKGLPGFKAG |
| SEQ ID NO: 12 | Pseudomonas aeruginosa | pyocin AP41 immunity protein | BAA02197 | DIKNNLSDYTESEFLEIIEEFFKNKSGLKGSELEKRMDKLVKHF EEVTSHPRKSGVIFHPKPGFETPEGIVKEVKEWRAANGLPGFKA G |
| SEQ ID NO: 13 | Salmonella enterica | bacteriocin immunity protein | YP_152132 | KLKENISDYTESEFIDFLRVIFSENESDTDETLDPLLEYFEKIT EYPGGTDLIYYPETESDGTPEGILNIIKEWRESQGLPCFKKSK |
| SEQ ID NO: 14 | Pseudomonas putida | Pyocin S-type immunity protein | AAN66929 | SEKTKLSDYTENEFLALIIEIHRANLEEPDHVLGGLLDHFSKIT EHPSGYDLLYRPNPKENGKPEKVLEIVKQWRLANGKDGFKPS |
| SEQ ID NO: 15 | Salmonella enterica | bacteriocin immunity protein | YP_152133 | ELKNNLEDYTEDEFIEFLNNFFEPPEELTGDELSKFIDNLLRHF NKITQHPDGGDLIFYPSEEREDSPEGVIEELKRWRKSQRLPCFK ENK |

For use in the subject methods, native bacterial immunity proteins, for example as set forth in SEQ ID NO:1 to SEQ ID NO:15, or variants thereof may be used, where variants may comprise amino acid deletions, insertions or substitutions. Peptides of interest include fragments of at least about 45 contiguous amino acids, more usually at least about 50 contiguous amino acids, and may comprise 55 or more amino acids, up to the provided peptide. Deletions may extend from the amino terminus or the carboxy terminus of the protein, and may delete about 1, about 2, about 5, about 10, about 15 or more amino acids from either or both termini.

Substitutions or insertions may be made of 1, 2, 3, 4, 5, or more amino acids, where the substitutions may be conservative or non-conservative, so long as the fast folding and alpha-helical nature of the protein is not changed. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine). Such substitutions or insertions may introduce sequences useful as purification tags.

Optionally a linker peptide will be joined at one or both of the amino terminus and carboxy terminus with a short flexible linker, e.g. comprising at least about 2, 3, 4 or more glycine, serine and/or alanine residues. One such linker comprises the motif (GGGGS), and may be present in one or more copies.

Modifications of interest that do not alter primary sequence include chemical derivatization of polypeptides, e.g., acylation, pegylation, acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza, Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the antigen is a viral antigen. Viral polypeptide antigens include, but are not limited to, core proteins such as HIV gag proteins (including, but not limited to, membrane anchoring (MA) protein, core capsid (CA) protein and nucleocapsid (NC) protein), HIV polymerase, influenza virus matrix (M) protein, influenza hemaglutinin protein, and influenza virus nucleocapsid (NP) protein. References discussing influenza vaccination include Scherle and Gerhard (1988) Proc. Natl. Acad. Sci. USA 85:4446-4450; Scherle and Gerhard (1986) J. Exp. Med. 164:1114-1128; Granoff et al. (1993) Vaccine 11:S46-51; Kodihalli et al. (1997) J. Virol. 71:3391-3396; Ahmeida et al. (1993) Vaccine 11:1302-1309; Chen et al. (1999) Vaccine 17:653-659; Govorkova and Smirnov (1997) Acta Virol. (1997) 41:251-257; Koide et al. (1995) Vaccine 13:3-5; Mbawuike et al. (1994) Vaccine 12:1340-1348; Tamura et al. (1994) Vaccine 12:310-316; Tamura et al. (1992) Eur. J. Immunol. 22:477-481; Hirabayashi et al. (1990) Vaccine 8:595-599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with linker. Lea et al. (1996) Biochim. Biophys. Acta 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX®II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, micro-organisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) Hoppe Seylers Z. Physiol. Chem. 362: 833-839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation:

A Practical Approach, IRL Press. Peptides can also be isolated using standard techniques such as affinity chromatography.

Preferably the antigens are peptides, lipids (e.g., sterols, fatty acids, and phospholipids), polysaccharides such as those used in *H. influenza* vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

Fusion Protein Constructs

In some embodiments of the invention, a first polypeptide and a second polypeptide are joined through a bacterial immunity protein linker to form a fusion protein, or a bacterial immunity protein linker is joined to a first polypeptide to form a fusion protein. As used herein, the terms "fusion protein" or "fusion polypeptide" or grammatical equivalents herein are meant to denote a protein composed of a plurality of protein components, which are typically unjoined in their native state but are joined by their respective amino and carboxyl termini through a linker to form a single continuous polypeptide. "Protein" in this context includes proteins, polypeptides and peptides. Plurality in this context means at least two, and preferred embodiments generally utilize a first and a second polypeptide joined through a linker.

As outlined below, the fusion polypeptide (or fusion polynucleotide encoding the fusion polypeptide) can comprise further components as well, including multiple peptides at multiple loops, fusion partners, etc. The precise site at which the fusion is made is not critical; particular sites are well known and may be selected in order to optimize the biological activity, secretion or binding characteristics of the binding partner. The optimal site will be determined by routine experimentation.

The invention further provides nucleic acids encoding the fusion polypeptides of the invention. As will be appreciated by those in the art, due to the degeneracy of the genetic code, an extremely large number of nucleic acids may be made, all of which encode the fusion proteins of the present invention. Thus, having identified a particular amino acid sequence, those skilled in the art could make any number of different nucleic acids, by simply modifying the sequence of one or more codons in a way that does not change the amino acid sequence of the fusion protein.

Using the nucleic acids of the present invention that encode a fusion protein, a variety of expression constructs can be made. The expression constructs may be self-replicating extrachromosomal vectors or vectors which integrate into a host genome. Alternatively, for purposes of cell-free expression the construct may include those elements required for transcription and translation of the desired polypeptide, but may not include such elements as an origin of replication, selectable marker, etc. Cell-free constructs may be replicated in vitro, e.g. by PCR, and may comprise terminal sequences optimized for amplification reactions.

Generally, expression constructs include transcriptional and translational regulatory nucleic acid operably linked to the nucleic acid encoding the fusion protein. The term "control sequences" refers to DNA sequences necessary for the expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading phase. Linking is accomplished by ligation or through amplification reactions. Synthetic oligonucleotide adaptors or linkers may be used for linking sequences in accordance with conventional practice.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in in vitro expression systems, such as the T7 promoter.

In addition, the expression construct may comprise additional elements. For example, the expression vector may have one or two replication systems, thus allowing it to be maintained in organisms, for example in mammalian or insect cells for expression and in a procaryotic host for cloning and amplification. In addition the expression construct may contain a selectable marker gene to allow the selection of transformed host cells. Selection genes are well known in the art and will vary with the host cell used.

Cell-Free Synthesis

In some embodiments of the invention, the fusion protein; linker; and/or antigen is produced by cell-free, or in vitro synthesis, in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. A number of reaction chemistries for polypeptide synthesis can be used in the methods of the invention. For example, reaction chemistries are described in U.S. Pat. No. 6,337,191, issued Jan. 8, 2002, and U.S. Pat. No. 6,168,931, issued Jan. 2, 2001, herein incorporated by reference.

In some embodiments of the invention, cell free synthesis is performed in a reaction where oxidative phosphorylation is activated, e.g. the CYTOMIM™ system. The activation of the respiratory chain and oxidative phosphorylation is evidenced by an increase of polypeptide synthesis in the presence of $O_2$. In reactions where oxidative phosphorylation is activated, the overall polypeptide synthesis in presence of $O_2$ is reduced by at least about 40% in the presence of a specific electron transport chain inhibitor, such as HQNO, or in the absence of $O_2$. The reaction chemistry may be as described in international patent application WO 2004/016778, herein incorporated by reference.

The CYTOMIM™ environment for synthesis utilizes cell extracts derived from bacterial cells grown in medium containing glucose and phosphate, where the glucose is present initially at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as E. coli, using both defined and undefined sources of nutrients (see Sambrook, J., E. F. Fritsch, and T. Maniatis. 1989. Molecular Cloning: A Laboratory Manual, $2^{nd}$ edition. Cold Spring Harbor University Press, Cold Spring Harbor, N.Y. for examples of glucose containing media). Alternatively, the culture may be grown using a protocol in which the glucose is continually fed as required to maintain a high growth rate in either a defined or complex growth medium.

The template for cell-free protein synthesis can be either mRNA or DNA. Translation of stabilized mRNA or combined transcription and translation converts stored information into protein. The combined system, generally utilized with a bacterial extract, e.g. an Enterobacteriaceae extract, including E. coli, Erwinia, Pseudomonas, Salmonella, etc., continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome of the extract source cells.

Vesicles, either purified from the host organism or synthetic, may also be added to the system. These may be used to enhance protein synthesis and folding. This cytomim technology has been shown to activate processes that utilize membrane vesicles containing respiratory chain components for the activation of oxidative phosphorylation. The present methods may be used for cell-free expression to activate other sets of membrane proteins.

Synthetic systems of interest include the replication of DNA, which may include amplification of the DNA, the transcription of RNA from DNA or RNA templates, the translation of RNA into polypeptides, and the synthesis of complex carbohydrates from simple sugars.

The reactions may be large scale, small scale, or may be multiplexed to perform a plurality of simultaneous syntheses. Additional reagents may be introduced to prolong the period of time for active synthesis. Synthesized product is usually accumulated in the reactor and then is isolated and purified according to the usual methods for protein purification after completion of the system operation.

Of particular interest is the translation of mRNA to produce proteins, which translation may be coupled to in vitro synthesis of mRNA from a DNA template. Such a cell-free system will contain all factors required for the translation of mRNA, for example ribosomes, amino acids, tRNAs, aminoacyl synthetases, elongation factors and initiation factors. Cell-free systems known in the art include E. coli extracts, etc., which can be treated with a suitable nuclease to eliminate active endogenous mRNA.

In addition to the above components such as cell-free extract, genetic template, and amino acids, materials specifically required for protein synthesis may be added to the reaction. These materials include salts, polymeric compounds, cyclic AMP, inhibitors for protein or nucleic acid degrading enzymes, inhibitors or regulators of protein synthesis, oxidation/reduction adjusters, non-denaturing surfactants, buffer components, putrescine, spermine, spermidine, etc.

The salts preferably include potassium, magnesium, and ammonium salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol, ascorbic acid, cysteine, glutathione and/or their oxides. Also, a non-denaturing surfactant such as Brij-35 may be used at a concentration of 0-0.5 M. Spermine and spermidine or optionally, in combination, putrescine may be used for improving protein synthetic ability, and cAMP may be used as a gene expression regulator.

Other salts, particularly those that are biologically relevant, such as manganese, may also be added. Potassium is generally added between 50-250 mM and ammonium between 0-100 mM. The pH of the reaction is generally between pH 6 and pH 9. The temperature of the reaction is generally between 20° C. and 40° C. These ranges may be extended.

When changing the concentration of a particular component of the reaction medium, that of another component may be changed accordingly. For example, the concentrations of several components such as nucleotides and energy source compounds may be simultaneously controlled in accordance with the change in those of other components. Also, the concentration levels of components in the reactor may be varied over time.

Preferably, the reaction is maintained in the range of pH 5-10 and a temperature of 20°-50° C., and more preferably, in the range of pH 6-9 and a temperature of 25°-40° C.

The amount of protein produced in a translation reaction can be measured in various fashions. One method relies on the availability of an assay which measures the activity of the particular protein being translated. Examples of assays for measuring protein activity are a luciferase assay system, and a chloramphenical acetyl transferase assay system. These assays measure the amount of functionally active protein produced from the translation reaction. Activity assays will not measure full-length protein that is inactive due to improper protein folding or lack of other post translational modifications necessary for protein activity.

Another method of measuring the amount of protein produced in a combined in vitro transcription and translation reactions is to perform the reactions using a known quantity of radiolabeled amino acid such as $^{35}S$-methionine or $^{14}C$-leucine and subsequently measuring the amount of radiolabeled amino acid incorporated into the newly translated protein. Incorporation assays will measure the amount of radiolabeled amino acids in all proteins produced in an in vitro translation reaction including truncated protein products. The radiolabeled protein may be further separated on a protein gel, and by autoradiography confirmed that the product is the proper size and that secondary protein products have not been produced.

Formulations

The compositions of the invention, especially useful to administering to an individual in need of immune stimulation (in the context of, for example, infectious disease, cancer, and allergy) generally comprise any of the polypeptide populations described herein in a sufficient amount to modulate an immune response.

Generally, the compositions of the invention preferably also comprise a pharmaceutically acceptable excipient, and may be in various formulations. As is well known in the art, a pharmaceutically acceptable excipient is a relatively inert substance that facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington's Pharmaceutical Sciences 19th Ed. Mack Publishing (1995).

Other formulations include suitable delivery forms known in the art including, but not limited to, carriers such as liposomes. Mahato et al. (1997) Pharm. Res. 14:853-859. Liposomal preparations include, but are not limited to, cytofectins, multilamellar vesicles and unilamellar vesicles.

Generally, these compositions are formulated for administration by injection or inhalation, e.g., intraperitoneally, intravenously, subcutaneously, intramuscularly, etc. Accordingly, these compositions are preferably combined with pharmaceutically acceptable vehicles such as saline, Ringer's solution, dextrose solution, and the like. The particular dosage regimen, i.e., dose, timing and repetition, will depend on the particular individual and that individual's medical history.

In some embodiments, more than one antigen(s) may be present in a composition. Such compositions may contain at least one, at least two, at least three, at least four, at least five, or more different antigen(s). Such "cocktails", as they are often denoted in the art, may be particularly useful in immunizing against pathogens present in different variants, e.g. HIV, rotavirus, influenza, etc.

Generally, the efficacy of administering any of these compositions is adjusted by measuring any change in the immune response as described herein, or other clinical parameters.

In some embodiments, the invention provides compositions comprising polypeptides as described herein and an adjuvant whereby the polypeptide(s)/adjuvant are co-administered. The immunogenic composition may contain an amount of an adjuvant sufficient to potentiate the immune response to the immunogen. Adjuvants are known in the art and include, but are not limited to, oil-in-water emulsions, water-in oil emulsions, alum (aluminum salts), liposomes and microparticles including but not limited to, polystyrene, starch, polyphosphazene and polylactide/polyglycosides. Other suitable adjuvants also include, but are not limited to, MF59, DETOX™ (Ribi), squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873-875, as well as, lipid-based adjuvants and others described herein. For veterinary use and for production of antibodies in animals, mitogenic components of Freund's adjuvant (both complete and incomplete) can be used.

In some embodiments, the immunity protein linker-antigen populations described herein can be administered in conjunction with one or more immunomodulatory facilitators. Thus, the invention provides compositions comprising linker-antigen conjugate populations and an immunomodulatory facilitator. As used herein, the term "immunomodulatory facilitator" refers to molecules which support and/or enhance the immunomodulatory activity of an immunity protein linker. Examples of immunomodulatory facilitators can include co-stimulatory molecules, such as cytokines, and/or adjuvants. The association of the linker and the facilitator molecules in a linker-facilitator conjugate can be through covalent interactions and/or through non-covalent interactions, including high affinity and/or low affinity interactions. Examples of non-covalent interactions that can couple an immunity protein linker and a facilitator include, but are not limited to, ionic bonds, hydrophobic interactions, hydrogen bonds and van der Waals attractions.

Immunomodulatory facilitators include, but are not limited to, co-stimulatory molecules (such as cytokines, chemokines, targeting protein ligand, trans-activating factors, peptides, and peptides comprising a modified amino acid) and adjuvants (such as alum, lipid emulsions, and polylactide/polyglycolide microparticles).

Among suitable immunomodulatory cytokine peptides for administration with linker are the interleukins (e.g., IL-1, IL-2, IL-3, etc.), interferons (e.g., IFN-α, IFN-β, IFN-γ), erythropoietin, colony stimulating factors (e.g., G-CSF, M-CSF, GM-CSF) and TNF-α. Preferably, immunostimulatory peptides for use in conjunction with linker oligonucleotides are those that stimulate Th1-type immune responses, such as IL-12 (Bliss et al. (1996) J. Immunol. 156:887-894), IL-18, TNF-α, β and γ, and/or transforming growth factor (TGF)-α.

The invention also provides compositions which comprise immunity protein linker-antigen compositions in conjunction with colloidal dispersion systems, such as microspheres, beads, macromolecular complexes, nanocapsules and lipid-based system, such as oil-in-water emulsions, micelles, mixed micelles and liposomes. Colloidal dispersion systems can provide effective encapsulation of linker-containing compositions. The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Administration and Assessment of the Immune Response

The immunity protein linker-antigen composition can be administered in combination with other pharmaceutical and/or immunogenic and/or immunostimulatory agents and can be combined with a physiologically acceptable carrier thereof.

As with all immunogenic compositions, the immunologically effective amounts and method of administration of the particular immunity protein linker-antigen formulation can vary based on the individual, what condition is to be treated and other factors evident to one skilled in the art. Factors to be considered include the antigenicity, whether or not the immunity protein linker-antigen composition will be complexed with or covalently attached to an adjuvant or delivery molecule, route of administration and the number of immunizing doses to be administered. Such factors are known in the art and it is well within the skill of immunologists to make such determinations without undue experimentation. A suitable dosage range is one that provides the desired modulation of immune response to the antigen. Generally, a dosage range of the immunity protein linker-antigen composition may be, for example, from about any of the following: 0.01 to 100 µg, 0.01 to 50 µg, 0.01 to 25 µg, 0.01 to 10 µg, 1 to 500 µg, 100 to 400 µg, 200 to 300 µg, 1 to 100 µg, 100 to 200 µg, 300 to 400 µg, 400 to 500 µg. Alternatively, the doses can be about any of the following: 0.1 µg, 0.25 µg, 0.5 µg, 1.0 µg, 2.0 µg, 5.0 µg, 10 µg, 25 µg, 50 µg, 75 µg, 100 µg. Accordingly, dose ranges can be those with a lower limit about any of the following: 0.1 µg, 0.25 µg, 0.5 µg and 1.0 µg; and with an upper limit of about any of the following: 250 µg, 500 µg and 1000 µg. In these compositions, the molar ratio of immunity protein linker to antigen may vary. The absolute amount given to each patient depends on pharmacological properties such as bioavailability, clearance rate and route of administration.

The effective amount and method of administration of the particular linker-antigen formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. The absolute amount given to each patient depends on pharmacological properties such as bioavailability, clearance rate and route of administration.

Parenteral routes of administration include but are not limited to electrical (iontophoresis) or direct injection such as direct injection into a central venous line, intravenous, intramuscular, intraperitoneal, intradermal, or subcutaneous injection. Compositions suitable for parenteral administration include, but are not limited, to pharmaceutically acceptable sterile isotonic solutions. Such solutions include, but are not limited to, saline and phosphate buffered saline for injection of the linker-containing compositions.

Naso-pharyngeal and pulmonary routes of administration include, but are not limited to, inhalation, transbronchial and transalveolar routes. The invention includes linker/antigen-containing compositions suitable for administration by inhalation including, but not limited to, various types of aerosols for inhalation, as well as powder forms for delivery systems. Devices suitable for administration by inhalation of linker/antigen-containing compositions include, but are not limited to, atomizers and vaporizers. Atomizers and vaporizers filled with the powders are among a variety of devices suitable for use in inhalation delivery of powders.

The methods of producing suitable devices for injection, topical application, atomizers and vaporizers are known in the art and will not be described in detail.

The above-mentioned compositions and methods of administration are meant to describe but not limit the methods of administering the linker/antigen-containing compositions of the invention. The methods of producing the various compositions and devices are within the ability of one skilled in the art and are not described in detail here.

Analysis (both qualitative and quantitative) of the immune response to linker/antigen-containing compositions can be by any method known in the art, including, but not limited to, measuring antigen-specific antibody production (including measuring specific antibody subclasses), activation of specific populations of lymphocytes such as CD4+ T cells or NK cells, production of cytokines such as IFNγ, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Serum concentrations of cytokines can be measured, for example, by ELISA. These and other assays to evaluate the immune response to an immunogen are well known in the art. See, for example, Selected Methods in Cellular Immunology (1980) Mishell and Shiigi, eds., W.H. Freeman and Co.

In some instances, a Th1 or Th2-type response is stimulated, i.e., elicited and/or enhanced. With reference to the invention, stimulating a Th1 or Th2-type immune response can be determined in vitro or ex vivo by measuring cytokine production from cells treated with linker as compared to those treated without linker. Methods to determine the cytokine production of cells include those methods described herein and any known in the art. The type of cytokines produced in response to treatment indicates a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-γ. In contrast, "Th2-type biased cytokines" refers to those associated with a Th2-type immune response, and include, but are not limited to, IL-4, IL-5, and IL-13. Cells useful for the determination of linker activity include cells of the immune system, primary cells isolated from a host and/or cell lines, usually APCs and lymphocytes.

Methods of the Invention

The invention also includes methods of modulating an immune response comprising administering an immunogenic formulation as described herein to an individual in an amount sufficient to modulate the immune response. Generally, the individual is in need of, or will be in need of, such modulation, due, for example, for a disease condition or being at risk of developing a disease condition. Examples of disease conditions include, but are not limited to, allergy, cancer, infectious diseases (such as viral or bacterial infection).

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

The bacterial immunity protein Im9 protein was inserted between the domains of a GMCSF-ScFv (Single-Chain Variable Fragment composed of 38C13 $V_L$ and 38C13 $V_H$) fusion protein. By using Im9 either as a linker between GM-CSF and the 38C13 ScFv (a ScFv derived from the 38C13 IgM on the surface of the 38C13 B cell lymphoma) or attached to the ScFv without GM-CSF, the fusion proteins become better vaccines. These two Im9 fusion proteins are more effective at generating a specific immune response against the 38C13 IgM than either version lacking Im9. Furthermore, mice immunized with fusion proteins containing the Im9 fusion protein are better able to reject subsequent tumor challenge with the 38C13 tumor.

The level of antibodies (Abs) specific to the native 38C13 protein in the serum of mice immunized with cell-free vaccine composed of a 38C13-derived ScFv was determined. The ability of Im9 fusion proteins to induce antibodies was tested by two separate assays. The first, an ELISA (Enzyme-Linked Immunosorbant Assay) measures the level of Abs against a soluble protein, in this case the 38C13 IgM. The second, and most representative of the type of Abs needed to target the actual tumor, is flow cytometry. This measures the level of antibodies against a cellular target, in this case, the 38C13 IgM on the tumor cell.

By both of the above assays, it was found that the inclusion of Im9 to the ScFv made it a more effective immunogen. Using an ELISA assay, it was found that the Im9 containing polypeptides, either as an internal or a terminal linker, induced a much higher 38C13-specific antibody titer in immunized mice ($p=0.0042$ and 0.0002 respectively) after 3 vaccinations (FIG. 1). These results were consistent with measurements that assessed antibody binding to 38C13 cells. By flow cytometry, it was also found that Im9 increased the ability of mice to make Abs specific to the 38C13 tumor, an important test of Ab specificity in determining the humoral effect on tumors. After 3 vaccinations, Im9-38ScFv induced higher anti-tumor Ab levels than 38ScFv alone ($p=0.0002$) and GM-Im9-ScFv greater than GM-ScFv alone ($p<0.0001$) (FIG. 2).

Taken together, these results demonstrate an increased immunogenic effect from the inclusion of Im9 to an antigen of interest, with or without the immunomodulatory protein GM-CSF.

Of particular interest is the role of Im9 in making the vaccines better at eliciting a response resulting in tumor rejection. Fourteen days following the $3^{rd}$ vaccination with the cell-free vaccines, mice were challenged with 1200 38C13 tumor cells. 38C13 is the B cell lymphoma model from which the 38C13 idiotype was derived. Mice immunized with proteins containing Im9 had significantly increased survival in response to 38C13 tumor challenge (FIG. 3). Those mice immunized with Im9-38ScFv, had much better survival rates than those who got 38ScFv alone. Likewise, mice that received GM-Im9-ScFv were better protected than those getting GM-ScFv without Im9. These results clearly demonstrate the ability of Im9 to increase the efficacy of cell-free ScFv vaccines in promoting immunity able to reject subsequent tumor challenge.

Materials and Methods

Protein Production. Protein for in vivo mouse experiments was produced using a protocol according to the methods in Yang et al., *Expression of active murine granulocyte-macrophage colony-stimulating factor in an Escherichia coli cell-free system. Biotechnol Prog,* 2004. 20(6): p. 1689-96. Some modifications were made in order to produce a larger quantity needed for mouse immunizations. Reaction volumes with 30 ml total reaction volume was used to produce the protein for mouse experiments. This protein was produced without the addition of $^{14}$C-Leucine. The reaction mixture was placed as a large drop in a petri dish (with five ml in each of six dishes) and incubated at 30° C. for 4 hr. After 4 hr., the soluble protein was separated by centrifugation at 15,000×g for 15 min. The soluble fraction was loaded on a 5 ml Ni-NTA column (Qiagen), which was pre-equilibrated with 50 mM phosphate buffer (pH 8.0) containing 300 mM NaCl and 10 mM imidazole. The column was then washed with 30 ml 25 mM imidazole in the same buffer and eluted with the same buffer solution but containing 250 mM imidazole. The purified products were then concentrated and dialyzed against PBS buffer. Finally, the vaccine protein was brought to a concentration of 0.1% Tween-20 and sterilized by filtration through a 0.2 μM filter (Nalgene). The vaccines were kept at 4° C. for up to 5 weeks before vaccination.

Vaccine protein quantification. Following protein purification, vaccine proteins were quantified using a coomassie-stained SDS-Page gel (Invitrogen NuPage 10% Bis-Tris) under reducing conditions, by comparison against a BSA standard. 8 ul of purified protein or BSA standard (Pierce) of varying concentration was loaded along with dithiothreitol (DTT) and NuPage sample buffer (Invitrogen) in a final volume of 20 μl. Protein concentration was determined by comparing the relative intensity of purified vaccine products to BSA standards of known concentration.

Immunization with In Vitro fusion proteins and Id-KLH and Tumor Challenge. Mice (C3H/Hen) were vaccinated intraperitoneally (I.P.) with 15 μg of the appropriate ScFv, or the molar equivalent of the ScFv fusion proteins, diluted into 500 μl of PBS. Mice were vaccinated on day 0, 14, and 28 and tail-bled 10 days following the $3^{rd}$ vaccination to assay immune responses. Two weeks following the $3^{rd}$ vaccination, mice were challenged with 1200 38C13 cells intraperitoneally (I.P.) in 200 μl of PBS. Before tumor challenge, cells were thawed, washed 3× in RPMI/10% FCS/Pen-Strep/L-Glutamine/2ME and grown in culture for 3 days. Before tumor challenge, cells were washed 3× in PBS, then diluted to the correct concentration in PBS for injection Immunoassays for measurement of anti-tumor immune responses. To assay the humoral immune response in the 38C13 tumor model, we used an ELISA (Enzyme-Linked Immunosorbant Assay) to quantify the level of 38C13-specific IgG produced by mice in response to vaccination, as well as FACS staining to assess the ability of the vaccine-induced Ab response to recognize the 38C13 tumor. For the ELISA, 96-well flat-bottom Maxisorp Immunoplates (Nunc) were coated with 5 ug/ml 38C13 Ab in carbonate buffer overnight. The following day, the plates were blocked with 5% non-fat milk in PBS, serum (from C3H/Hen mice 10 days post $3^{rd}$ vaccination) or standard (anti 38C13 Id of 4 different isotypes) was diluted in 1% BSA/PBS and applied for 1 h, and bound IgG from serum was detected using a Goat-anti-Mouse IgG-specific HRP-conjugated Ab (Southern Biotech). Plates were washed 4× in between steps with ELISA wash buffer (PBS/NaCl/Triton X), and detection was performed with ABTS chromogenic substrate (Roche) and observed by measuring OD 405-490 with a Kinetic Microplate Reader (Molecular Devices).

FACS staining was performed using 38C13 cells to test responses to 38C13 vaccines. Cells were grown in RPMI, washed in PBS w/1% BSA, 0.05% Sodium Azide, and resuspended in the same buffer to be aliquoted to 500,000 cells/tube. Cells were contacted with serum for 30 min at a 1:800 dilution, washed 2× in FACS buffer, then stained with FITC-conjugated Goat-anti-Mouse IgG. The cells were analyzed on a FACScalibur flow cytometry machine (Becton Dickinson).

Example 2

The hemagglutinin extraviral domain or hemagglutinin receptor binding site domain was fused to GM-CSF connected by a normal GGGGS (SEQ ID NO:16) linker and an Im9 linker. For the purpose of animal testing, mouse GM-CSF was used, although the human sequence is readily used in its place. The following fusion proteins constructs have been made Table 2 DNA sequences of HA fusion protein domains

TABLE 2

DNA sequences of HA fusion protein domains

| | Description | Sequence |
|---|---|---|
| 5'CAT | The 5' of CAT, first 15 bp | ATGGAGAAAAAAATC (SEQ ID NO:17) |
| 6 His | His Tag, 6 histidines | CATCACCACCATCACCAC (SEQ ID NO:18) |
| G4S | Small linker | GGTGGTGGTGGCTCC (SEQ ID NO:19) |
| GMCSF | granulocyte-macrophage colony-stimulating factor, 124 amino acids | GCTCCGACCCGCAGCCCTATCACGGTGACTCGTCCGTGGAAA CATGTGGAAGCTATCAAAGAGGCTCTGAACCTGCTGGATGAC ATGCCGGTCACTCTGAACGAGGAAGTTGAAGTTGTTTCCAAC GAGTTCTCCTTCAAAAAGCTGACCTGTGTCCAGACCCGTCTG AAAATTTTCGAACAGGGCCTGCGTGGCAACTTCACCAAGCTG AAAGGTGCTCTGAACATGACCGCGTCTTACTACCAAACTTAT TGCCCGCCGACGCCAGAAACCGACTGCGAAACCCAGGTGACG ACTTACGCGACTTCATCGACTCCCTGAAAACCTTTCTGACG GACATCCCGTTTGAATGCAAGAAACCAGTCCAGAAA (SEQ ID NO:20) |
| IM9 | Im 9. It contains four α-helices in its structure and folds very quickly, 85 amino acids | GAACTGAAGCACAGCATTTCTGACTACACTGAAGCCGAGTTC CTGCAACTGGTAACCACCATCTGCAACGCCGATACTTCTTCT GAAGAAGAACTGGTAAAACTGGTTACTCACTTCGAGGAGATG ACCGAACATCCGTCTGGTAGCGACCTGATCTATTACCCGAAG GAAGGTGATGATGATAGCCCTTCTGGCATCGTAAACACGGTA AAGCAATGGCGCGCAGCTAACGGCAAATCTGGCTTCAAACAG GGT (SEQ ID NO:21) |
| HA RBS (Hong Kong) | Receptor binding site of HA, Hong Kong, 232 amino acids | CTGTGCGACCTGAACGGTGTAAAGCCGCTGATCCTGCGTGAC TGCTCTGTCGCTGGCTGGCTGCTGGGCAACCCGATGTGTGAC GAGTTCATTAACGTGCCGGAGTGGTCCTATATCGTAGAGAAA GCCAGCCCGGCAAATGATCTGTGTTACCCGGGCAACTTTAAC GACTACGAAGAACTGAAACACCTGCTGTCCCGCATCAATCAT TTTGAGAAAATCCAGATTATCCCTAAAAGCTCTTGGTCTAAC CACGATGCGAGCAGCGGTGTTTCCAGCGCATGCCCGTACCTG GGTCGCTCCTCCTTCTTCCGTAACGTTGTATGGCTGATTAAG AAAAACAGCGCATACCCAACGATCAAACGTTCCTACAACAAC ACCAATCAGGAAGATCTGCTGGTGCTGTGGGGTGTTCATCAC CCGAACGACGCTGCGGAGCAGACCAAACTGTATCAGAACCCG ACCACCTATATCAGCGTTGGCACCTCTACCCTGAACCAGCGT CTGGTGCCGGAAATCGCCACCCGTCCGAAGGTGAACGGTCAG TCTGGCCGTATGGAGTTCTTCTGGACGATCCTGAAGCCGAAC GATGCGATCAATTTCGAATCTAACGGCAACTTCATCGCGCCG GAATACGCATACAAAATTGTTAAAAAGGGTGATTCCACTATT ATGAAGTCCGAACTGGAGTACGGT (SEQ ID NO:22) |
| HA (Viet Nam) | Viet Nam 1203/04, 567 amino acids | GAAAAGATCGTTCTGCTGTTTGCAATCGTGTCTCTGGTAAAA AGCGATCAAATTTGTATCGGTTACCACGCTAACAACTCCACT GAACAGGTGGATACCATCATGGAGAAAAACGTTACTGTGACT CACGCCCAGGATATTCTGGAAAAGAAACACAACGGTAAGCTG TGTGACCTGGACGGTGTTAAGCCGCTGATCCTGCGTGACTGT |

TABLE 2-continued

DNA sequences of HA fusion protein domains

| Description | | Sequence |
|---|---|---|
| | | TCTGTCGCTGGCTGGCTGCTGGGTAACCCAATGTGTGATGAG<br>TTTATCAACGTTCCTGAATGGAGCTACATTGTGGAAAAAGCG<br>AACCCAGTCAACGATCTGTGTTATCCGGGTGACTTCAACGAC<br>TATGAAGAACTGAAACATCTGCTGTCCCGTATTAACCACTTC<br>GAAAAGATCCAGATCATCCCGAAAAGCTCCTGGTCTAGCCAT<br>GAAGCATCCCTGGGCGTCAGCTCTGCGTGCCCTTACCAGGGC<br>AAATCCAGCTTCTTTCGTAACGTTGTCTGGCTGATTAAAAAG<br>AACTCCACTTACCCGACCATTAAACGCAGCTACAACAACACT<br>AACCAGGAAGATCTGCTGGTCCTGTGGGGTATCCATCACCCG<br>AACGACGCGGCAGAACAGACCAAGCTGTATCAGAACCCGACT<br>ACCTACATTAGCGTTGGTACCTCCACCCTGAACCAACGCCTG<br>GTTCCGCGCATCGCAACTCGTTCTAAAGTGAACGGCCAGTCC<br>GGCCGCATGGAATTTTTCTGGACTATCCTGAAACCGAACGAC<br>GCTATTAACTTCGAGTCCAACGGCAACTTTATTGCACCGGAA<br>TACGCCTACAAAATTGTTAAGAAAGGTGACTCCACTATTATG<br>AAATCTGAACTGGAATACGGTAACTGCAACACTAAATGTCAG<br>ACCCCAATGGGTGCCATCAACTCCTCCATGCCGTTCCATAAC<br>ATCCACCCGCTGACGATTGGTGAATGTCCGAAATATGTAAAA<br>AGCAACCGTCTGGTACTGGCCACTGGTCTGCGCAACTCTCCG<br>CAGCGTGAACGCCGTCGTAAGAAACGTGGTCTGTTTGGTGCG<br>ATCGCTGGCTTTATCGAGGGCGGTTGGCAGGGCATGGTAGAC<br>GGCTGGTACGGCTACCACCACAGCAACGAACAGGGCTCTGGT<br>TACGCGGCGGATAAAGAAAGCACGCAAAAAGCGATCGACGGC<br>GTTACCAACAAAGTTAACAGCATTATCGATAAGATGAATACC<br>CAGTTTGAAGCGGTTGGTCGTGAATTCAATAACCTGGAGCGC<br>CGCATCGAAAACCTGAACAAAAAGATGGAAGATGGTTTTCTG<br>GACGTCTGGACCTATAACGCTGAACTGCTGGTGCTGATGGAA<br>AATGAACGCACCCTGGATTTCCACGACAGCAACGTGAAAAAT<br>CTGTACGACAAAGTACGTCTGCAGCTGCGTGATAACGCGAAG<br>GAACTGGGCAACGGTTGTTTCGAATTTTACCATAAGTGCGAC<br>AACGAATGTATGGAATCCGTTCGCAACGGCACCTATGACTAC<br>CCGCAGTACTCTGAAGAAGCCCGTCTGAAACGCGAGGAAATC<br>TCTGGTGTTAAACTGGAATCCATCGGTATTTACCAAATCCTG<br>AGCATTTATTCCACCGTGGCTTCTTCTCTGGCCCTGGCGATC<br>ATGGTTGCGGGCCTGAGCCTGTGGATGTGCAGCAACGGTTCT<br>CTGCAGTGTCGTATTTGCATC (SEQ ID NO:23) |
| HA RBS (Viet Nam) | Receptor binding site of HA, Viet Nam 1203/04, 232 amino acids | TGTGACCTGGACGGTGTTAAGCCGCTGATCCTGCGTGACTGT<br>TCTGTCGCTGGCTGGCTGCTGGGTAACCCAATGTGTGATGAG<br>TTTATCAACGTTCCTGAATGGAGCTACATTGTGGAAAAAGCG<br>AACCCAGTCAACGATCTGTGTTATCCGGGTGACTTCAACGAC<br>TATGAAGAACTGAAACATCTGCTGTCCCGTATTAACCACTTC<br>GAAAAGATCCAGATCATCCCGAAAAGCTCCTGGTCTAGCCAT<br>GAAGCATCCCTGGGCGTCAGCTCTGCGTGCCCTTACCAGGGC<br>AAATCCAGCTTCTTTCGTAACGTTGTCTGGCTGATTAAAAAG<br>AACTCCACTTACCCGACCATTAAACGCAGCTACAACAACACT<br>AACCAGGAAGATCTGCTGGTCCTGTGGGGTATCCATCACCCG<br>AACGACGCGGCAGAACAGACCAAGCTGTATCAGAACCCGACT<br>ACTTACATTAGCGTTGGTACCTCCACCCTGAACCAACGCCTG<br>GTTCCGCGCATCGCAACTCGTTCTAAAGTGAACGGCCAGTCC<br>GGCCGCATGGAATTTTTCTGGACTATCCTGAAACCGAACGAC<br>GCTATTAACTTCGAGTCCAACGGCAACTTTATTGCACCGGAA<br>TACGCCTACAAAATTGTTAAGAAAGGTGACTCCACTATTATG<br>AAATCTGAACTGGAATACGGTAAC (SEQ ID NO:24) |

These original and new constructs are expressed in the cell-free protein synthesis system (Calhoun and Swartz, 2005, Biotechnology Progress 21:1146). The standard cell-free reaction mixture used in this work includes 13.3 µg/ml of DNA template, 20 mM magnesium glutamate, 10 mM ammonium glutamate, 170 mM potassium glutamate, 1.2 mM AMP, 0.86 mM GMP, 0.86 mM UMP, 0.86 mM CMP, 34 µg/mL folinic acid, 170.6 µg/mL E. coli tRNA, 20 amino acids (2 mM for each), 0.03 M phosphoenolpyruvate (PEP), 0.33 mM NAD, 0.27 mM CoA, 2.69 mM oxalic acid, 4.2 µM $^{14}$C-Leucine, 0.07 mg/mL T7 RNA polymerase, 1.5 mM spermidine, 1.0 mM putrescine and 24% (v/v) S30 extract.

To eliminate disulfide reducing activity, cell extract was mixed with 1 mM iodoacetamide and incubated at room temperature for 30 minutes prior to being added to the cell-free reaction mixture. 4 mM oxidized glutathione, 1 mM reduced glutathione, and 100 µg/mL DsbC were added to reaction mixtures before template DNA addition to enhance disulfide bond formation and protein folding (5).

S30 cell extract was prepared from E. coli K12 strain KC6 (Calhoun and Swartz, 2006, Journal of Biotechnology, 123: 193) according to the high density fermentation procedures (Zawada and Swartz, 2005, Biotechnology and Bioengineering 89:407; Liu et al., 2005, Biotechnology Progress 21:460). To get a relatively oxidized environment, no $_{DL}$-dithiothreitol was added to the cell lysate after homogenization. T7 RNA polymerase was prepared from the culture of E. coli strain BL21 (pAR1219) according to the procedures of Davanloo et al (1984). E. coli DsbC was prepared from strain BL21(DE3) (pETDsbChisC) and was purified with a Q Sepharose column.

The amount of synthesized protein was estimated from the measured TCA-precipitated radioactivities in a liquid scintillation counter. After centrifuging samples at 4° C., 15000 RCF, for 15 minutes, supernatants were taken and used to determine soluble yield by TCA precipitation and scintillation counting.

Figure 4:
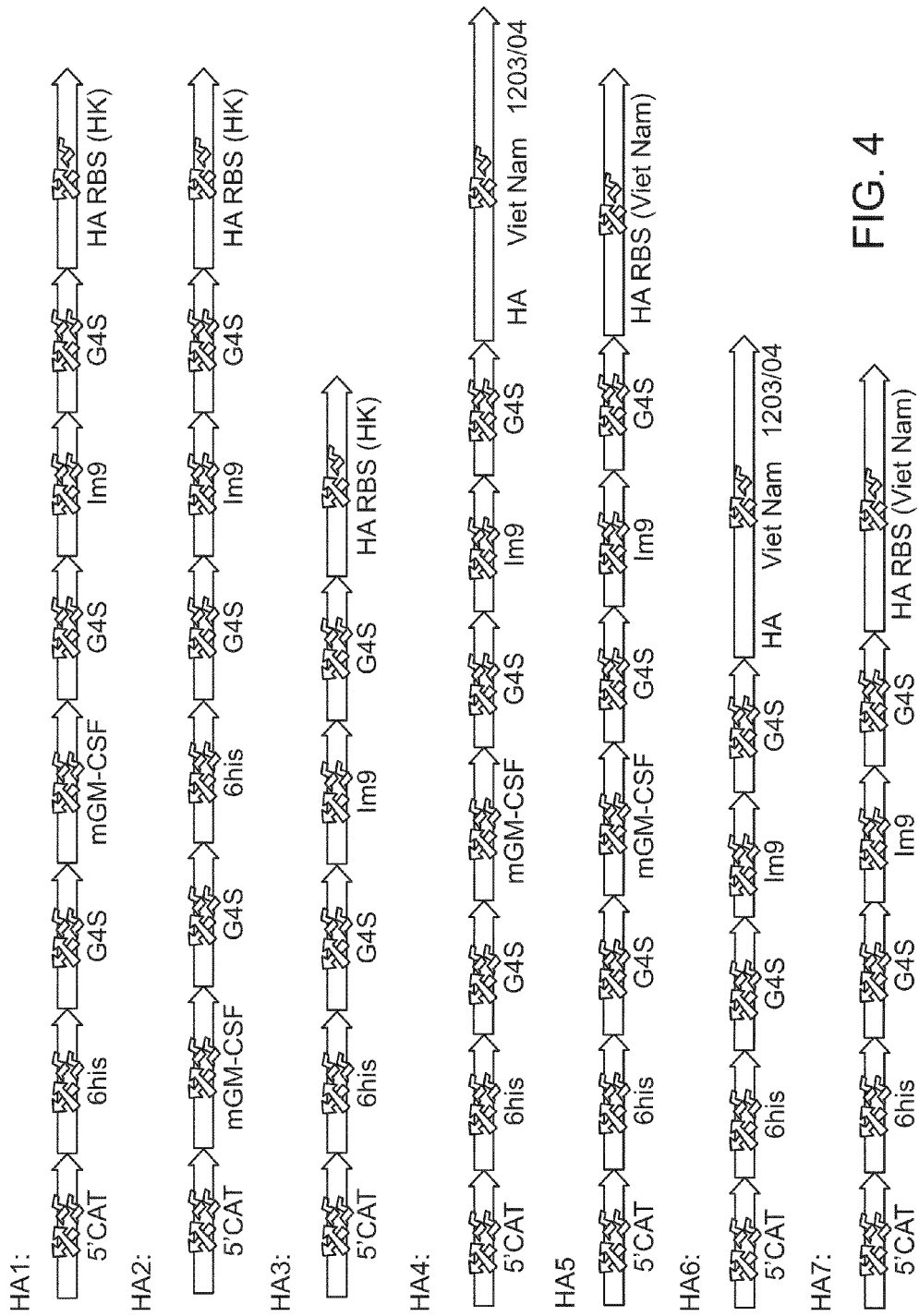
Figure 5:
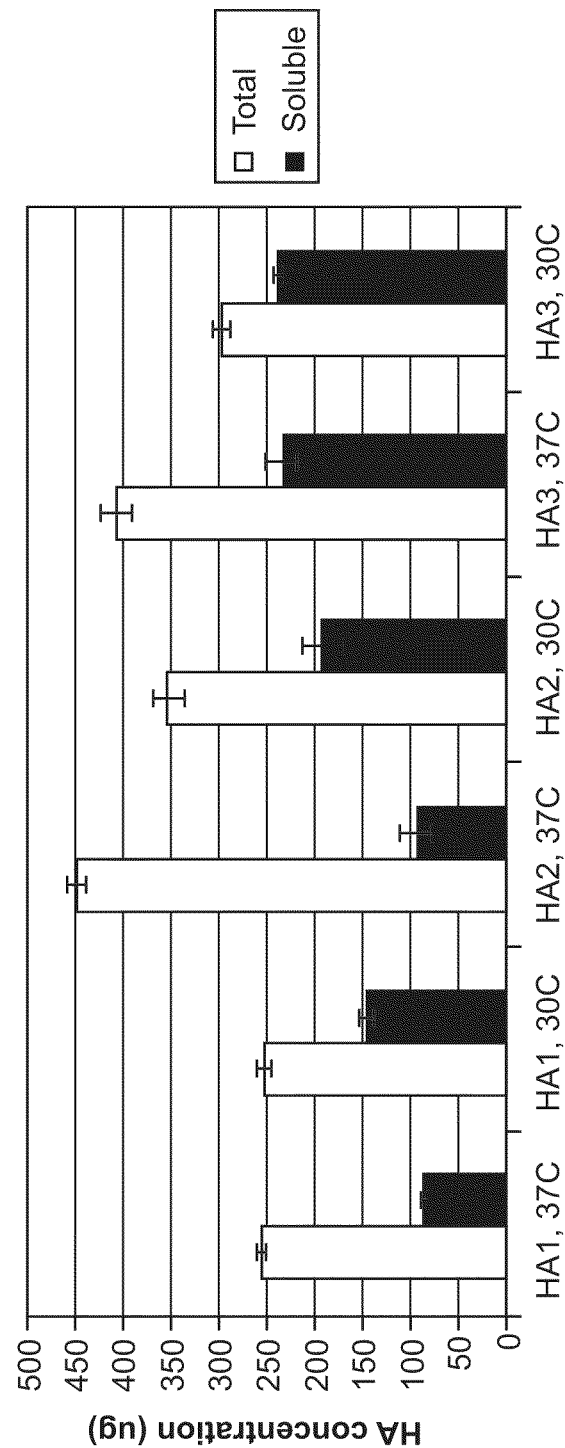
Figure 6:
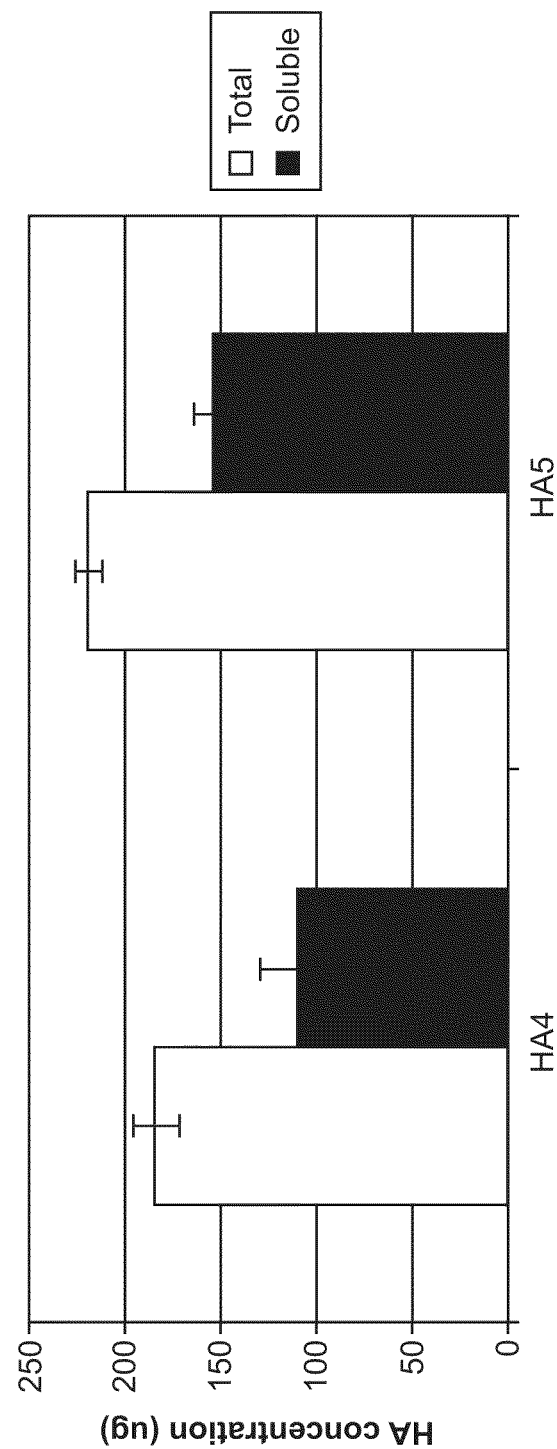

FIG. 4 shows diagrams of the various influenza vaccine candidates that were produced. Expression yields are shown in FIGS. 5 and 6 and in Table 3. Data demonstrate the feasibility of producing such fusion proteins in the cell-free system.

The cell-free system produces more soluble HA fusion protein at 30 C than 37 C. Lower temperature slows product aggregation in the cell-free system. The total and soluble yields at 30 C of HA constructs are listed in the table below:

TABLE 3

The production yields of HA constructs

| | Molecular weight KD | Total yield ug/mL | Soluble yield ug/mL |
|---|---|---|---|
| HA1 | 52 | 250 | 145 |
| HA2 | 52 | 350 | 190 |
| HA3 | 38 | 280 | 240 |
| HA4 | 90 | 180 | 110 |
| HA5 | 52 | 220 | 150 |

Figure 7:
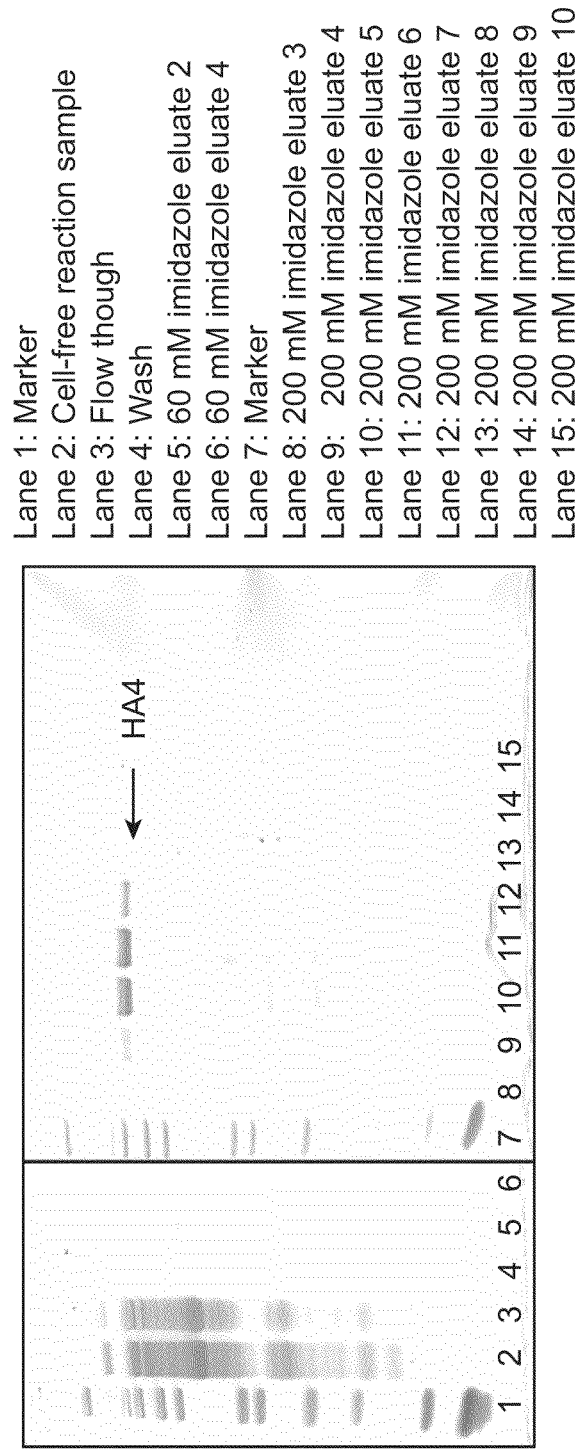

HA4 and HA5 were purified with a HisTrap column, since the fusion proteins have N terminal His tags. The product was eluted with imidazole solution in phosphate buffer, pH 7.3. The SDS PAGE results are shown in FIGS. 7 and 8 and demonstrate that the HA4 and HA5 fusion protein can be isolated from other cell-free materials by HisTrap column purification and that the fusion proteins remain intact through the production and purification process.

Example 3

The following example is provided to demonstrate the effectiveness of the compositions of the invention as vaccines. The example provides two fusion protein constructs with an influenza hemagglutinin (HA) polypeptide fused to the bacterial immunity protein Im9. These two constructs, HA fusion protein (HA6) and HA RBS fusion protein (HA7), are illustrated in FIG. 1 and differ only in the length of the HA polypeptide. As demonstrated below, both fusion proteins were able to confer protection from influenza virus in mice. Viet Nam HA (HA6) and HA RBS (HA7) Cell-Free Expression:

The fusion proteins were produced by cell-free reactions done at 30 C for 4 hours using the modified cytomim system described in Example 1. The total yields of synthesized HA6 and HA7 were 180 and 220 ug/mL, 110 and 160 ug/mL of which were soluble, respectively.

HA6 and HA7 Purification:

His-tagged HA6 and HA7 were purified with a HisTrap column (see FIG. 1). To generate product for mouse study, 10 mL cell-free reaction for each construct was made in the form of thin film in a petri dish at 30 C for 4 hours. The sample was then centrifuged at 15,000×g for 15 min at 4 C. The soluble fraction was loaded on 1 mL Histrap column, which was pre-equilibrated with 50 mM phosphate buffer (pH 7.3) containing 500 mM NaCl and 10 mM imidazole. The product was eluted with 60 mM and 200 mM imidazole solution in phosphate buffer, pH 7.3 by step-wise elution method. Each fraction contained 0.45 mL eluate. SDS-PAGE gels were stained with Invitrogen Simplyblue Safestain as shown in FIG.?. For the HA6 sample, fractions 4, 5, 6 and 7 of 60 mM imidazole eluates were collected, pooled and buffer changed against PBS buffer by ultrafiltration spin columns (Vivaspin, 10,000 MWCO). For HA7, fractions of 60 mM imidazole eluates 4-8 and fractions of 200 mM imidazole eluates 1~3 were collected, pooled and buffer changed against PBS buffer by ultrafiltration spin columns (Vivaspin, 10,000 MWCO).

The T7 RNA polymerase used in the cell-free reaction was also His tagged. Therefore, T7 RNA polymerase was also present in the samples.

Mouse Study Results:

The samples were sent to St. Jude Children's Research Hospital for mouse study, which was carried out by Dr. Richard Webby. The negative control was His tagged T7 RNA polymerase. The positive control was derived from inactivated influenza viral particles provided by Dr. Webby. Eight days after challenge with active influenza virus, the following results were observed:

Positive control: 5 of 5 mice alive

Negative control: 1 of 5 mice alive (survivor did not look healthy)

HA7: 5 of 5 mice alive

HA6: 2 of 5 mice alive.

HA7 protected all of the influenza-challenged mice from death. Both HA6 and HA7 constructs conferred protection compared to the negative control. HA7 was produced at a higher level in the cell-free system, possibly because it is a shorter construct than HA6 (see FIG. 1). Thus, there was more HA7 protein relative to T7 RNA polymerase in the HA7 sample than in the HA6 sample.

What is claimed is:

1. A method for immunization, the method comprising: administering to a mammalian host an antigenic formulation comprising an antigen of interest and a bacterial immunity protein or fragment thereof wherein said bacterial immunity protein is a polypeptide of from 55 to 90 amino acids in length, having 4 α helices in a distorted, antiparallel four-helical structure, and lacking disulphide bonds; and wherein said antigen of interest is a polypeptide that is covalently bonded to the bacterial immunity protein.

2. The method according to claim 1, wherein said bacterial immunity protein is internally fused to said antigen of interest.

3. The method according to claim 1, wherein said bacterial immunity protein is terminally fused to said antigen of interest.

4. The method of claim 1, wherein the antigen is an influenza protein.

5. The method of claim 4, wherein the influenza protein is an influenza A HA protein.

6. The method of claim 1, wherein the bacterial immunity protein is a colicin binding protein.

7. The method of claim 1, wherein the bacterial immunity protein has at least 95% sequence identity with a polypeptide set forth in any one of SEQ ID NO:1-15.

8. A method of increasing the immunogenicity of an antigen, the method comprising: formulating said antigen for administration to a mammalian host with a bacterial immunity protein or fragment thereof wherein said bacterial immunity protein is a polypeptide of from 55 to 90 amino acids in length, having 4 α helices in a distorted, antiparallel four-helical structure, and lacking disulphide bonds; and wherein said antigen of interest is a polypeptide that is covalently bonded to the bacterial immunity protein.

* * * * *

SEQUENCE LISTING

```
<160> NUMBER OF SEQ ID NOS: 24

<210> SEQ ID NO 1
<211> LENGTH: 85
<212> TYPE: PRT
<213> ORGANISM: Escherichia coli

<400> SEQUENCE: 1

Glu Leu Lys His Ser Ile Ser Asp Tyr Thr Glu Ala Glu Phe Leu Gln
 1               5                   10                  15

Leu Val Thr Thr Ile Cys Asn Ala Asp Thr Ser Ser Glu Glu Glu Leu
            20                  25                  30

Val Lys Leu Val Thr His Phe Glu Glu Met Thr Glu His Pro Ser Gly
        35                  40                  45
```

```
Ser Asp Leu Ile Tyr Tyr Pro Lys Glu Gly Asp Asp Ser Pro Ser
        50                  55                  60

Gly Ile Val Asn Thr Val Lys Gln Trp Arg Ala Ala Asn Gly Lys Ser
65                  70                  75                  80

Gly Phe Lys Gln Gly
                85
```

<210> SEQ ID NO 2
<211> LENGTH: 84
<212> TYPE: PRT
<213> ORGANISM: Escherichia coli

<400> SEQUENCE: 2

```
Gly Leu Lys Leu His Ile Asn Trp Phe Asp Lys Arg Thr Glu Phe
1               5                   10                  15

Lys Gly Gly Glu Tyr Ser Lys Asp Phe Gly Asp Gly Ser Val Ile
                20                  25                  30

Glu Arg Leu Gly Met Pro Phe Lys Asp Asn Ile Asn Asn Gly Trp Phe
            35                  40                  45

Asp Val Ile Ala Glu Trp Val Pro Leu Leu Gln Pro Tyr Phe Asn His
        50                  55                  60

Gln Ile Asp Ile Ser Asp Asn Glu Tyr Phe Val Ser Phe Asp Tyr Arg
65                  70                  75                  80

Asp Gly Asp Trp
```

<210> SEQ ID NO 3
<211> LENGTH: 82
<212> TYPE: PRT
<213> ORGANISM: Escherichia coli

<400> SEQUENCE: 3

```
Lys Leu Ser Pro Lys Ala Ala Ile Glu Val Cys Asn Glu Ala Ala Lys
1               5                   10                  15

Lys Gly Leu Trp Ile Leu Gly Ile Asp Gly Gly His Trp Leu Asn Pro
                20                  25                  30

Gly Phe Arg Ile Asp Ser Ser Ala Ser Trp Thr Tyr Asp Met Pro Glu
            35                  40                  45

Glu Tyr Lys Ser Lys Ile Pro Glu Asn Asn Arg Leu Ala Ile Glu Asn
        50                  55                  60

Ile Lys Asp Asp Ile Glu Asn Gly Tyr Thr Ala Phe Ile Ile Thr Leu
65                  70                  75                  80

Lys Met
```

<210> SEQ ID NO 4
<211> LENGTH: 85
<212> TYPE: PRT
<213> ORGANISM: Escherichia coli

<400> SEQUENCE: 4

```
Glu Leu Lys His Ser Ile Ser Asp Tyr Thr Glu Ala Glu Phe Leu Glu
1               5                   10                  15

Phe Val Lys Lys Ile Cys Arg Ala Glu Gly Ala Thr Glu Glu Asp Asp
                20                  25                  30

Asn Lys Leu Val Arg Glu Phe Glu Arg Leu Thr Glu His Pro Asp Gly
            35                  40                  45

Ser Asp Leu Ile Tyr Tyr Pro Arg Asp Asp Arg Glu Asp Ser Pro Glu
        50                  55                  60
```

Gly Ile Val Lys Glu Ile Lys Glu Trp Arg Ala Ala Asn Gly Lys Pro
65 70 75 80

Gly Phe Lys Gln Gly
85

<210> SEQ ID NO 5
<211> LENGTH: 86
<212> TYPE: PRT
<213> ORGANISM: Escherichia coli

<400> SEQUENCE: 5

Glu Leu Lys Asn Ser Ile Ser Asp Tyr Thr Glu Ala Glu Phe Val Gln
1 5 10 15

Leu Leu Lys Glu Ile Glu Lys Glu Asn Val Ala Ala Thr Asp Asp Val
20 25 30

Leu Asp Val Leu Leu Glu His Phe Val Lys Ile Thr Glu His Pro Asp
35 40 45

Gly Thr Asp Leu Ile Tyr Tyr Pro Ser Asp Asn Arg Asp Asp Ser Pro
50 55 60

Glu Gly Ile Val Lys Glu Ile Lys Glu Trp Arg Ala Ala Asn Gly Lys
65 70 75 80

Pro Gly Phe Lys Gln Gly
85

<210> SEQ ID NO 6
<211> LENGTH: 95
<212> TYPE: PRT
<213> ORGANISM: Yersinia pestis

<400> SEQUENCE: 6

Lys Phe Ile Gln Asp Val Glu Glu Asn Lys Met Glu Leu Lys Glu Lys
1 5 10 15

Tyr Glu Asp Tyr Thr Glu His Glu Phe Leu Glu Phe Ile Arg Asn Ile
20 25 30

Cys Glu Val Asn Thr Asp Ser Gln Ser Leu His Ser Ser Trp Val Arg
35 40 45

His Phe Thr Lys Ile Thr Glu His Pro Ser Gly Ser Asp Leu Ile Tyr
50 55 60

Tyr Pro Glu Asp Gly Ala Asp Asp Ser Pro Glu Gly Ile Leu Glu Leu
65 70 75 80

Val Lys Lys Trp Arg Ala Glu Asn Gly Lys Pro Gly Phe Lys Lys
85 90 95

<210> SEQ ID NO 7
<211> LENGTH: 84
<212> TYPE: PRT
<213> ORGANISM: Escherichia coli

<400> SEQUENCE: 7

Glu Leu Lys Asn Ser Ile Ser Asp Tyr Thr Glu Thr Glu Phe Lys Lys
1 5 10 15

Ile Ile Glu Asp Ile Ile Asn Cys Glu Gly Asp Glu Lys Lys Gln Asp
20 25 30

Asp Asn Leu Glu His Phe Ile Ser Val Thr Glu His Pro Ser Gly Ser
35 40 45

Asp Leu Ile Tyr Tyr Pro Glu Gly Asn Asn Asp Gly Ser Pro Glu Ala
50 55 60

Val Ile Lys Glu Ile Lys Glu Trp Arg Ala Ala Asn Gly Lys Ser Gly
65 70 75 80

```
<210> SEQ ID NO 8
<211> LENGTH: 84
<212> TYPE: PRT
<213> ORGANISM: Photorhabdus luminescens

<400> SEQUENCE: 8

Lys Leu Asn Lys Lys Leu Glu Asp Tyr Thr Glu Ala Glu Phe Leu Glu
 1               5                  10                  15

Phe Ala Arg Lys Val Cys Asn Ala Asp Tyr Ala Thr Glu Asp Glu Ala
            20                  25                  30

Asn Val Ala Val Gln Asp Phe Ile Arg Leu Ser Glu His Pro Asp Gly
        35                  40                  45

Thr Asp Ile Leu Phe Tyr Pro Ser Ser Gly Gln Asp Ser Pro Glu
    50                  55                  60

Gly Ile Val Lys Gln Ile Lys Glu Trp Arg Ala Lys Ser Gly Lys Pro
65                  70                  75                  80

Gly Phe Lys Lys

<210> SEQ ID NO 9
<211> LENGTH: 84
<212> TYPE: PRT
<213> ORGANISM: Klebsiella pneumoniae

<400> SEQUENCE: 9

Ala Asn Lys Thr Leu Ala Asp Tyr Thr Glu Gln Glu Phe Ile Glu Phe
 1               5                  10                  15

Ile Glu Lys Ile Lys Lys Ala Asp Phe Ala Thr Glu Ser Glu His Asp
            20                  25                  30

Glu Ala Ile Tyr Glu Phe Ser Gln Leu Thr Glu His Pro Asp Gly Trp
        35                  40                  45

Asp Leu Ile Tyr His Pro Gln Ala Gly Ala Asp Asn Ser Pro Ala Gly
    50                  55                  60

Val Val Lys Thr Val Lys Glu Trp Arg Ala Ala Asn Gly Lys Pro Gly
65                  70                  75                  80

Phe Lys Lys Ser

<210> SEQ ID NO 10
<211> LENGTH: 83
<212> TYPE: PRT
<213> ORGANISM: Yersinia pseudotuberculosis

<400> SEQUENCE: 10

Glu Asp Lys Ser Ile Cys Asp Tyr Thr Glu Ser Glu Phe Leu Glu Leu
 1               5                  10                  15

Val Lys Glu Leu Phe Asn Val Glu Lys Thr Thr Glu Glu Asp Ile
            20                  25                  30

Asn Asn Leu Ile Glu Phe Lys Arg Leu Cys Glu His Pro Ala Gly Ser
        35                  40                  45

Asp Leu Ile Phe Tyr Pro Asp Asn Asn Arg Glu Asp Ser Pro Glu Gly
    50                  55                  60

Val Val Lys Glu Val Lys Lys Trp Arg Ala Glu Asn Gly Lys Pro Gly
65                  70                  75                  80

Phe Lys Lys

<210> SEQ ID NO 11
```

<211> LENGTH: 86
<212> TYPE: PRT
<213> ORGANISM: Pseudomonas aeruginosa

<400> SEQUENCE: 11

Lys Ser Lys Ile Ser Glu Tyr Thr Glu Lys Glu Phe Leu Glu Phe Val
1               5                   10                  15

Glu Asp Ile Tyr Thr Asn Asn Lys Lys Lys Phe Pro Thr Glu Glu Ser
            20                  25                  30

His Ile Gln Ala Val Leu Glu Phe Lys Lys Leu Thr Glu His Pro Ser
        35                  40                  45

Gly Ser Asp Leu Leu Tyr Tyr Pro Asn Glu Asn Arg Glu Asp Ser Pro
50                  55                  60

Ala Gly Val Val Lys Glu Val Lys Glu Trp Arg Ala Ser Lys Gly Leu
65                  70                  75                  80

Pro Gly Phe Lys Ala Gly
                85

<210> SEQ ID NO 12
<211> LENGTH: 89
<212> TYPE: PRT
<213> ORGANISM: Pseudomonas aeruginosa

<400> SEQUENCE: 12

Asp Ile Lys Asn Asn Leu Ser Asp Tyr Thr Glu Ser Glu Phe Leu Glu
1               5                   10                  15

Ile Ile Glu Glu Phe Phe Lys Asn Lys Ser Gly Leu Lys Gly Ser Glu
            20                  25                  30

Leu Glu Lys Arg Met Asp Lys Leu Val Lys His Phe Glu Glu Val Thr
        35                  40                  45

Ser His Pro Arg Lys Ser Gly Val Ile Phe His Pro Lys Pro Gly Phe
50                  55                  60

Glu Thr Pro Glu Gly Ile Val Lys Glu Val Lys Glu Trp Arg Ala Ala
65                  70                  75                  80

Asn Gly Leu Pro Gly Phe Lys Ala Gly
                85

<210> SEQ ID NO 13
<211> LENGTH: 87
<212> TYPE: PRT
<213> ORGANISM: Salmonella enterica

<400> SEQUENCE: 13

Lys Leu Lys Glu Asn Ile Ser Asp Tyr Thr Glu Ser Glu Phe Ile Asp
1               5                   10                  15

Phe Leu Arg Val Ile Phe Ser Glu Asn Glu Ser Asp Thr Asp Glu Thr
            20                  25                  30

Leu Asp Pro Leu Leu Glu Tyr Phe Glu Lys Ile Thr Glu Tyr Pro Gly
        35                  40                  45

Gly Thr Asp Leu Ile Tyr Tyr Pro Gly Thr Glu Ser Asp Gly Thr Pro
50                  55                  60

Glu Gly Ile Leu Asn Ile Ile Lys Glu Trp Arg Glu Ser Gln Gly Leu
65                  70                  75                  80

Pro Cys Phe Lys Lys Ser Lys
                85

<210> SEQ ID NO 14
<211> LENGTH: 86
<212> TYPE: PRT

<213> ORGANISM: Pseudomonas putida

<400> SEQUENCE: 14

```
Ser Glu Lys Thr Lys Leu Ser Asp Tyr Thr Glu Asn Glu Phe Leu Ala
1               5                   10                  15

Leu Ile Ile Glu Ile His Arg Ala Asn Leu Glu Pro Asp His Val
            20                  25                  30

Leu Gly Gly Leu Leu Asp His Phe Ser Lys Ile Thr Glu His Pro Ser
        35                  40                  45

Gly Tyr Asp Leu Leu Tyr Arg Pro Asn Pro Lys Glu Asn Gly Lys Pro
    50                  55                  60

Glu Lys Val Leu Glu Ile Val Lys Gln Trp Arg Leu Ala Asn Gly Lys
65                  70                  75                  80

Asp Gly Phe Lys Pro Ser
                85
```

<210> SEQ ID NO 15
<211> LENGTH: 91
<212> TYPE: PRT
<213> ORGANISM: Salmonella enterica

<400> SEQUENCE: 15

```
Glu Leu Lys Asn Asn Leu Glu Asp Tyr Thr Glu Asp Glu Phe Ile Glu
1               5                   10                  15

Phe Leu Asn Asn Phe Phe Glu Pro Pro Glu Glu Leu Thr Gly Asp Glu
            20                  25                  30

Leu Ser Lys Phe Ile Asp Asn Leu Arg His Phe Asn Lys Ile Thr
        35                  40                  45

Gln His Pro Asp Gly Gly Asp Leu Ile Phe Tyr Pro Ser Glu Glu Arg
    50                  55                  60

Glu Asp Ser Pro Glu Gly Val Ile Glu Glu Leu Lys Arg Trp Arg Lys
65                  70                  75                  80

Ser Gln Arg Leu Pro Cys Phe Lys Glu Asn Lys
                85                  90
```

<210> SEQ ID NO 16
<211> LENGTH: 5
<212> TYPE: PRT
<213> ORGANISM: Artificial Sequence
<220> FEATURE:
<223> OTHER INFORMATION: Synthetic linker peptide

<400> SEQUENCE: 16

```
Gly Gly Gly Gly Ser
1               5
```

<210> SEQ ID NO 17
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 17
atggagaaaa aaatc                                                    15

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide

```
<400> SEQUENCE: 18
catcaccacc atcaccac                                                   18

<210> SEQ ID NO 19
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 19
ggtggtggtg gctcc                                                      15

<210> SEQ ID NO 20
<211> LENGTH: 372
<212> TYPE: DNA
<213> ORGANISM: Artificial Sequence
<220> FEATURE:
<223> OTHER INFORMATION: Synthetic polynucleotide

<400> SEQUENCE: 20
gctccgaccc gcagccctat cacggtgact cgtccgtgga acatgtgga agctatcaaa       60 gaggctctga acctgctgga tgacatgccg gtcactctga cgaggaagt tgaagttgtt      120 tccaacgagt tctccttcaa aaagctgacc tgtgtccaga cccgtctgaa aattttcgaa     180
cagggcctgc gtggcaactt caccaagctg aaaggtgctc tgaacatgac cgcgtcttac    240
taccaaactt attgcccgcc gacgccagaa accgactgcg aaacccaggt gacgacttac    300
gcggacttca tcgactccct gaaaaccttt ctgacggaca tcccgtttga atgcaagaaa   360
ccagtccaga aa                                                        372

<210> SEQ ID NO 21
<211> LENGTH: 255
<212> TYPE: DNA
<213> ORGANISM: Artificial Sequence
<220> FEATURE:
<223> OTHER INFORMATION: Synthetic polynucleotide

<400> SEQUENCE: 21
gaactgaagc acagcatttc tgactacact gaagccgagt tcctgcaact ggtaaccacc     60
atctgcaacg ccgatacttc ttctgaagaa gaactggtaa aactggttac tcacttcgag   120
gagatgaccg aacatccgtc tggtagcgac ctgatctatt acccgaagga aggtgatgat   180
gatagccctt ctggcatcgt aaacacggta agcaatggc gcgcagctaa cggcaaatct     240
ggcttcaaac agggt                                                    255

<210> SEQ ID NO 22
<211> LENGTH: 696
<212> TYPE: DNA
<213> ORGANISM: Artificial Sequence
<220> FEATURE:
<223> OTHER INFORMATION: Synthetic polynucleotide

<400> SEQUENCE: 22
ctgtgcgacc tgaacggtgt aaagccgctg atcctgcgtg actgctctgt cgctggctgg     60
ctgctgggca acccgatgtg tgacgagttc attaacgtgc cggagtggtc ctatatcgta    120
gagaaagcca gcccggcaaa tgatctgtgt tacccgggca actttaacga ctacgaagaa    180
ctgaaacacc tgctgtcccg catcaatcat tttgagaaaa tccagattat ccctaaaagc    240
tcttggtcta accacgatgc gagcagcggt gtttccagcg catgcccgta cctgggtcgc    300
```

```
tcctccttct tccgtaacgt tgtatggctg attaagaaaa acagcgcata cccaacgatc      360
aaacgttcct acaacaacac caatcaggaa gatctgctgg tgctgtgggg tgttcatcac      420
ccgaacgacg ctgcggagca gaccaaactg tatcagaacc cgaccaccta tatcagcgtt      480
ggcacctcta ccctgaacca gcgtctggtg ccggaaatcg ccacccgtcc gaaggtgaac      540
ggtcagtctg gccgtatgga gttcttctgg acgatcctga agccgaacga tgcgatcaat      600
ttcgaatcta acggcaactt catcgcgccg gaatacgcat acaaaattgt taaaaagggt      660
gattccacta ttatgaagtc cgaactggag tacggt                                696

<210> SEQ ID NO 23
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 23
gaaaagatcg ttctgctgtt tgcaatcgtg tctctggtaa aaagcgatca aatttgtatc       60
ggttaccacg ctaacaactc cactgaacag gtggatacca tcatggagaa aaacgttact      120
gtgactcacg cccaggatat tctggaaaag aaacacaacg gtaagctgtg tgacctggac      180
ggtgttaagc cgctgatcct gcgtgactgt tctgtcgctg ctggctgctg ggtaacccca      240
atgtgtgatg agtttatcaa cgttcctgaa tggagctaca ttgtggaaaa agcgaaccca      300
gtcaacgatc tgtgttatcc gggtgacttc aacgactatg aagaactgaa acatctgctg      360
tcccgtatta accacttcga aaagatccag atcatcccga aaagctcctg gtctagccat      420
gaagcatccc tgggcgtcag ctctgcgtgc ccttaccagg gcaaatccag cttctttcgt      480
aacgttgtct ggctgattaa aaagaactcc acttacccga ccattaaacg cagctacaac      540
aacactaacc aggaagatct gctggtcctg tggggtatcc atcacccgaa cgacgcggca      600
gaacagacca gctgtatca gaacccgact acctacatta gcgttggtac ctccacccctg      660 aaccaacgcc tggttccgcg catcgcaact cgttctaaag tgaacggcca gtccggccgc      720
atggaatttt tctggactat cctgaaaccg aacgacgcta ttaacttcga gtccaacggc      780
aactttattg caccggaata cgcctacaaa attgttaaga aggtgactc cactattatg      840 aaatctgaac tggaatacgg taactgcaac actaaatgtc agaccccaat gggtgccatc      900
aactcctcca tgccgttcca taacatccac ccgctgacga ttggtgaatg tccgaaatat      960
gtaaaaagca accgtctggt actggccact ggtctgcgca actctccgca gcgtgaacgc     1020
cgtcgtaaga aacgtggtct gtttggtgcg atcgctggct ttatcgaggg cggttggcag     1080
ggcatggtag acggctggta cggctaccac cacagcaacg aacagggctc tggttacgcg     1140
gcggataaag aaagcacgca aaagcgatc gacggcgtta ccaacaaagt taacagcatt     1200
atcgataaga tgaatacca gtttgaagcg gttggtcgtg aattcaataa cctggagcgc     1260
cgcatcgaaa acctgaacaa aaagatggaa gatggttttc tggacgtctg gacctataac     1320
gctgaactgc tggtgctgat ggaaaatgaa cgcaccctgg atttccacga cagcaacgtg     1380
aaaaatctgt acgacaaagt acgtctgcag ctgcgtgata cgcgaagga actgggcaac     1440 ggttgtttcg aattttacca taagtgcgac aacgaatgta tggaatccgt tcgcaacggc     1500
acctatgact acccgcagta ctctgaagaa gcccgtctga aacgcgagga aatctctggt     1560
gttaaactgg aatccatcgg tatttaccaa atcctgagca tttattccac cgtggcttct     1620
tctctggccc tggcgatcat ggttgcgggc ctgagcctgt ggatgtgcag caacggttct     1680
```

-continued

```
ctgcagtgtc gtatttgcat c                                             1701

<210> SEQ ID NO 24
<211> LENGTH: 696
<212> TYPE: DNA
<213> ORGANISM: Artificial Sequence
<220> FEATURE:
<223> OTHER INFORMATION: Synthetic polynucleotide

<400> SEQUENCE: 24
tgtgacctgg acggtgttaa gccgctgatc ctgcgtgact gttctgtcgc tggctggctg     60
ctgggtaacc caatgtgtga tgagtttatc aacgttcctg aatggagcta cattgtggaa    120
aaagcgaacc cagtcaacga tctgtgttat ccgggtgact tcaacgacta tgaagaactg    180
aaacatctgc tgtcccgtat taaccacttc gaaaagatcc agatcatccc gaaaagctcc    240
tggtctagcc atgaagcatc cctgggcgtc agctctgcgt gcccttacca gggcaaatcc    300
agcttctttc gtaacgttgt ctggctgatt aaaaagaact ccacttaccc gaccattaaa    360
cgcagctaca acaacactaa ccaggaagat ctgctggtcc tgtggggtat ccatcacccg    420
aacgacgcgg cagaacagac caagctgtat cagaacccga ctacctacat tagcgttggt    480
acctccaccc tgaaccaacg cctggttccg cgcatcgcaa ctcgttctaa agtgaacggc    540
cagtccggcc gcatggaatt tttctggact atcctgaaac cgaacgacgc tattaacttc    600
gagtccaacg gcaactttat tgcaccggaa tacgcctaca aaattgttaa gaaaggtgac    660
tccactatta tgaaatctga actggaatac ggtaac                              696
```